United States Patent [19]

Artz

[11] Patent Number: 5,071,469
[45] Date of Patent: Dec. 10, 1991

[54] HERBICIDAL BENZYLSULFONAMIDES

[75] Inventor: Steven P. Artz, Wilmington, Del.

[73] Assignee: E. I. Du Pont de Nemours and Company, Wilmington, Del.

[21] Appl. No.: 465,753

[22] Filed: Jan. 24, 1990

Related U.S. Application Data

[63] Continuation-in-part of Ser. No. 342,214, Apr. 21, 1989, abandoned.

[51] Int. Cl.$^5$ ............... C07D 239/69; C07D 239/48; A01N 43/54
[52] U.S. Cl. ........................ 71/92; 544/321; 544/323; 544/332
[58] Field of Search ............ 71/92; 544/321, 323, 544/332

[56]  References Cited

U.S. PATENT DOCUMENTS

| 4,332,611 | 6/1982 | Petersen | 71/92 |
| 4,348,220 | 9/1982 | Schwing | 71/92 |
| 4,370,480 | 1/1983 | Levitt et al. | 544/320 |
| 4,420,325 | 12/1983 | Sauers | 71/92 |
| 4,592,776 | 6/1986 | van Gemert | 71/93 |
| 4,622,065 | 11/1986 | van Gemert | 71/93 |
| 4,659,369 | 4/1987 | Levitt | 71/92 |
| 4,666,501 | 5/1987 | Hay et al. | 71/90 |
| 4,678,498 | 7/1987 | Artz | 71/87 |
| 4,678,500 | 7/1987 | Hay et al. | 71/92 |
| 4,687,506 | 8/1987 | O'Grady | 71/92 |
| 4,690,705 | 9/1987 | Christensen | 71/90 |
| 4,699,649 | 10/1987 | Rorer | 71/90 |
| 4,705,556 | 11/1987 | Hanagan | 71/90 |
| 4,778,512 | 10/1988 | Wexler | 71/92 |
| 4,801,327 | 1/1989 | Christensen et al. | 71/92 |

Primary Examiner—John M. Ford

[57] ABSTRACT

This invention relates to certain herbicidal sulfonamides, agriculturally suitable compositions thereof and a method for their use as a general or selective preemergent or postemergent herbicide or as a plant growth regulant.

21 Claims, No Drawings

HERBICIDAL BENZYLSULFONAMIDES

CROSS-REFERENCE TO RELATED APPLICATION

This application is continuation-in-part of application Ser. No. 07/342,214, filed Apr. 21, 1989, now abandoned.

BACKGROUND OF THE INVENTION

This invention relates to certain herbicidal sulfonamides, agriculturally suitable compositions thereof and a method for their use as a general or selective preemergent or postemergent herbicide or as a plant growth regulant.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

The "sulfonylurea" herbicides are an extremely potent class of herbicides discovered within the last few years which generally consist of a sulfonylurea bridge, $-SO_2NHCONH-$, linking two aromatic or heteroaromatic rings.

U.S. Pat. No. 4,420,325 discloses, in part, herbicidal sulfonylureas of the formula

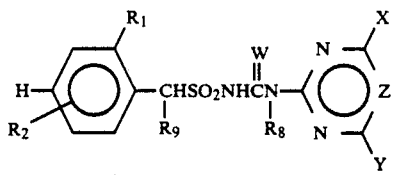

wherein:
R$_1$ is F, Cl, Br, CF$_3$, C$_1$-C$_3$ alkoxy, C$_1$-C$_3$ alkyl, NO$_2$, CO$_2$R$_4$, SO$_2$R$_5$, SO$_2$NR$_6$R$_7$, SO$_2$N(OCH$_3$)CH$_3$, SO$_2$OCH$_2$CF$_3$, OSO$_2$R$_5$ or CH$_2$L;
L is SO$_2$NR$_6$R$_7$, OCH$_3$, OC$_2$H$_5$, CO$_2$CH$_3$ or CO$_2$C$_2$H$_5$; and
R$_2$ is H, Cl, Br, F, CF$_3$ or OCH$_3$.

There is no disclosure in this reference of the compounds of the instant invention.

SUMMARY OF THE INVENTION

Now novel compounds, agriculturally suitable compositions containing them, and their method-of-use as preemergence and/or postemergence herbicides or plant growth regulants have been found. Accordingly compounds of the invention are compounds of the formula

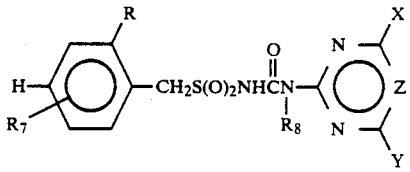

wherein
R is C(OH)R$_1$R$_2$, C(OR$_3$)R$_2$R$_4$, C(O)R$_1$ or C(OR$_5$)(OR$_6$)R$_4$;
R$_1$ is C$_1$-C$_3$ alkyl, C$_1$-C$_2$ haloalkyl or C$_1$-C$_2$ alkyl substituted by one of OCH$_3$, SCH$_3$ or CN;
R$_2$ is H or CH$_3$;
R$_3$ is C(O)(C$_1$-C$_3$ alkyl), C(O)cyclopropyl, S(O)$_2$(C$_1$-C$_3$ alkyl) or C(O)phenyl;
R$_4$ is H, C$_1$-C$_3$ alkyl, C$_1$-C$_2$ haloalkyl or C$_1$-C$_2$ alkyl substituted by one of OCH$_3$, SCH$_3$ or CN;
R$_5$ and R$_6$ are independently C$_1$-C$_2$ alkyl;
R$_7$ is H, CH$_3$, CF$_3$, F, Cl, Br, NO$_2$, OCH$_3$ or SCH$_3$;
R$_8$ is H or CH$_3$;
X is C$_1$-C$_2$ alkyl, C$_1$-C$_2$ alkoxy, C$_1$-C$_2$ haloalkoxy, CH$_2$OCH$_3$ or Cl;
Y is C$_1$-C$_2$ alkyl, C$_1$-C$_2$ alkoxy, NHCH$_3$ or N(CH$_3$)$_2$; and
Z is CH or N;
and their agriculturally suitable salts; provided that
a) when X is Cl, then Y is C$_1$-C$_2$ alkoxy, and Z is CH; and
b) when X is C$_1$ haloalkoxy, then Z is CH.

In the above definitions, the term "alkyl", used either alone or in compound words such as "haloalkyl", includes straight chain or branched alkyl, e.g., methyl, ethyl, n-propyl or isopropyl.

Alkoxy includes methoxy and ethoxy.

The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include CH$_2$CH$_2$F, CF$_2$CF$_3$ and CH$_2$CHFCl.

The total number of carbon atoms in a substituent group is indicated by the C$_i$-C$_j$ prefix where i and j are numbers from 1 to 3. For example, C$_1$-C$_3$ alkyl would designate methyl through propyl.

The compounds of the invention preferred for reasons including ease of synthesis and/or greater herbicidal efficacy are:

1. Compounds of Formula I wherein R$_9$ is H; X is CH$_3$ or OCH$_3$; and Y is CH$_3$ or OCH$_3$.
2. Compounds of Preferred 1 wherein R$_3$ is C(O)CH$_3$ or S(O)$_2$CH$_3$.
3. Compounds of Preferred 2 wherein R$_1$ is C$_1$-C$_3$ alkyl; R$_4$ is C$_1$-C$_3$ alkyl; and R$_7$ is H.

Compounds of the invention specifically preferred for reasons of greatest herbicidal efficacy, greatest safety to rice, and/or most favorable ease of synthesis are:

2-[1-(Acetyloxy)ethyl]-N-[[(4,6-dimethoxy-2-pyrimidinyl)amino]carbonyl]benzenemethanesulfonamide (R is C(OR$_3$)R$_2$R$_4$, R$_2$ is H, R$_3$ is C(O)CH$_3$, R$_4$ is CH$_3$, R$_7$ and R$_8$ are H, X and Y are OCH$_3$, and Z is CH; m.p. 68°-70° C.)

2-Acetyl-N-[[(4,6-dimethoxy-2-pyrimidinyl)-amino]-carbonyl]benzenemethanesulfonamide (R is C(O)R$_1$, R$_1$ is CH$_3$, R$_7$ and R$_8$ are H, X and Y are OCH$_3$, and Z is CH; m.p. 160°-163° C.(d)) and N-[[(4,6-dimethoxy-2-pyrimidinyl)amino]-carbonyl]-2-(1-hydroxyethyl)benzenemethanesulfonamide (R is C(OH)R$_1$R$_2$, R$_1$ is CH$_3$, R$_2$ is H, R$_7$ and R$_8$ are H, X and Y are OCH$_3$, and Z is CH; m.p. 147°-150° C.(d)).

This invention also comprises novel compounds, such as the benzylsulfonamides of Formula II, useful as intermediates for the preparation of compounds of Formula I

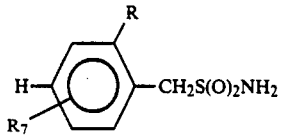

II wherein
R is C(OH)R$_1$R$_2$, C(OR$_3$)R$_2$R$_4$ or C(OR$_5$)(OR$_6$)R$_4$;
R$_1$ is C$_1$-C$_3$ alkyl, C$_1$-C$_2$ haloalkyl or C$_1$-C$_2$ alkyl substituted by one of OCH$_3$, SCH$_3$ or CN;
R$_2$ is H or CH$_3$;
R$_3$ is C(O)(C$_1$-C$_3$ alkyl); C(O)cyclopropyl, S(O)$_2$(-C$_1$-C$_3$ alkyl) or C(O)phenyl;
R$_4$ is H, C$_1$-C$_3$ alkyl, C$_1$-C$_2$ haloalkyl or C$_1$-C$_2$ alkyl substituted by one of OCH$_3$, SCH$_3$ or CN;
R$_5$ and R$_6$ are independently C$_1$-C$_2$ alkyl; and
R$_7$ is H, CH$_3$, CF$_3$, F, Cl, Br, NO$_2$, OCH$_3$ or SCH$_3$.

The compounds of the invention are highly active preemergent and/or postemergent herbicides or plant growth regulants. Some of the compounds of the invention are useful especially for the selective control of undesired vegetation in rice, wheat and barley crops.

DETAILED DESCRIPTION OF THE INVENTION

Synthesis

The sulfonylureas of Formula I can be prepared from other sulfonylureas of Formula I by one or more methods described in Equations 1a through 1g.

Equation 1a

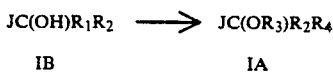

wherein

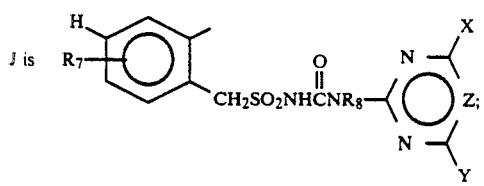

R$_1$, R$_2$, R$_3$, R$_5$, R$_6$, R$_7$, R$_8$, X, Y and Z are as previously defined; and R$_4$ is R$_1$.

The reaction of Equation 1a is best carried out with an anhydride, R$_3$OR$_3$, or a carboxylic acid chloride, R$_3$Cl, wherein R$_3$ is C(O)C$_1$-C$_3$ alkyl, C(O)cyclopropyl or C(O)phenyl, in the presence of a nitrogen base such as pyridine, triethylamine or preferably 4-N,N-dimethylaminopyridine. The reaction can be done in an inert solvent or neat in the case of anhydrides. The products can be isolated by extraction, crystalization or chromatography. Further description of ester formation can be found in Greene, "Protective Groups in Organic Synthesis", pp. 53-54, 61. Alkylsulfonates can be prepared by analogous methods, using a sulfonyl chloride, R$_3$Cl wherein R$_3$ is S(O)$_2$C$_1$-C$_3$ alkyl.

Equation 1b

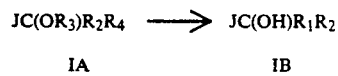

The reaction of Equation 1b is best carried out in water or an aqueous primary alcohol, such as methanol or ethanol, solution in the presence of a metal hydroxide such as sodium hydroxide, generally one to two equivalents. The hydroxyalkyl sulfonylurea, IB, is isolated after neutralization of the reaction mixture directly as a precipitate or extracted with an organic solvent such as ethyl acetate. Saponifications are well known and reviewed by Satchell and Satchell, in Patai, "The Chemistry of Carboxylic acids and Esters", pp. 375-452, Interscience Publishers, N.Y. (1969).

Equation 1c

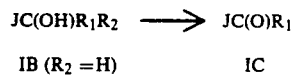

The reaction of Equation 1c can be carried out by a variety of oxidizing agents, including metals, such as MnO$_2$, pyridinium chlorochromate and Dess-Martin periodinane. The sulfonylurea is dissolved or suspended in an inert solvent, such as, dichloromethane, followed by the addition of the oxidizing agent. The product can be isolated by trituration, crystallization or chromatography. For a teaching of the periodinane reagent see *J. Org. Chem.*, 48 (1983) 4155.

Equation 1d

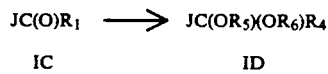

wherein
R$_1$ is as previously defined and R$_4$ is R$_1$.

The acetals and ketals of Formula ID can be prepared from the ketones of Formula IC by an acid-catalyzed exchange reaction with the appropriate acetone ketal according to the teachings of H. B. Lorette and W. L. Howard, *J. Org. Chem.*, 25 (1960), 521 as shown in Equation 1d. The aldehyde or ketone of Formula IC is treated with dimethyl acetone ketal with or without a cosolvent such as dichloromethane and an acid catalyst such as p-toluenesulfonic acid or boron trifluoride at, or above, ambient temperature. The acid catalyst is removed by washing with water, and the solvents are removed by distillation under reduced pressure.

Equation 1e

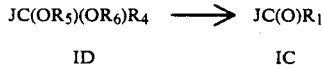

Ketals of Formula ID can be deprotected to the ketones of Formula IC, as shown in Equation 1e, by the use of an acid catalyst, such as Amberlyst-15 in wet acetone, wet silica gel or $CF_3CO_2H/CHCl_3-H_2O$, at ambient temperatures. The catalyst is filtered off and the solvent removed by distillation under reduced pressure. For additional teachings see Greene, "Protective Groups in Organic Synthesis", John Wiley and Sons, N.Y. (1981), pp. 116-120.

Equation 1f

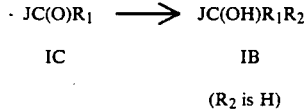

(R$_2$ is H)

The reaction of Equation 1f can be carried out by a variety of reduction procedures, including catalytic hydrogenation and reaction with metal hydrides such as lithium aluminum hydride, which are well known to one skilled in the art.

Equation 1g

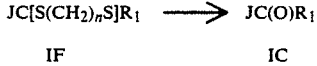

wherein:

R$_1$ is as previously defined and n is 2 or 3.

The dithiane, IF, can be converted to the ketone, IC, by treatment with mercury salts in aqueous acetone as shown in Equation 1g, according to the procedures reviewed by D. S. Tarbell and D. P. Harnish, *Chem. Rev.*, 49 (1950), 67.

Compounds of Formula I can be prepared by one or more of the procedures shown in Equations 2a; 2b and 2c.

Equation 2a

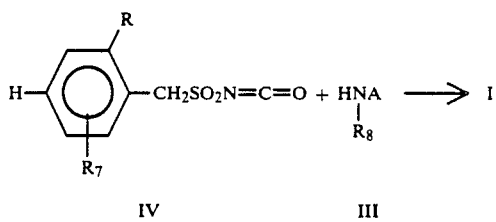

wherein:

R is $C(OR_3)R_2R_4$ or $C[S(CH_2)_nS]R_1$;

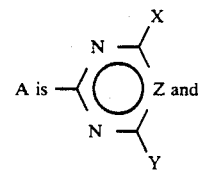

n, R$_7$ and R$_8$ are as previously defined.

The reaction of Equation 2a is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates are known in the art and are prepared from the corresponding sulfonamides (II) by one of the following two general methods.

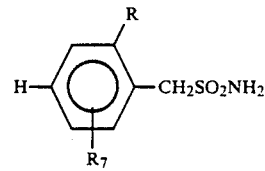

wherein

R is $C(OR_3)R_2R_4$ or $C[S(CH_2)_nS]R_1$ and

R$_7$ and n are as previously defined.

The sulfonamide II is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]-bicyclooctane (DABCO). The reaction mixture is heated to 135°-140° C. and held at that temperature for 5-60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, to give the sulfonyl isocyanate (IV).

If desired, the alkyl isocyanate-sulfonamide adduct can be made and isolated before reaction with the phosgene. In this case the sulfonamide (II), alkyl isocyanate, and anhydrous base (e.g., $K_2CO_3$) in polar, aprotic solvent (e.g., acetone, butanone, or acetonitrile) are mixed and heated under reflux for 1 to 6 hours. The reaction mixture is then diluted with water, and the pH is adjusted to about 3 with acid (e.g., HCl, $H_2SO_4$). The adduct is filtered out and dried, and then reacted with phosgene as described above. This procedure modification is especially useful when the sulfonamide (II) is high melting and has low solubility in the phosgenation solvent.

Many of the compounds of Formula I can be prepared by the procedure shown in Equation 2b.

Equation 2b

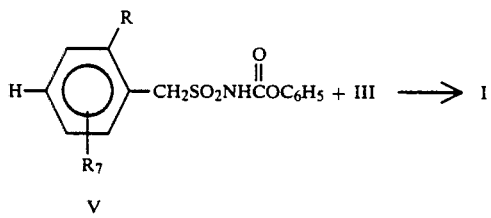

wherein
R is $CH(OH)R_1R_2$, $C(OR_3)R_2R_4$ or $C(OR_5)(OR_6)R_4$; and
$R_7$ is as previously defined.

The reaction of Equation 2b is carried out by contacting phenylcarbamates of Formula V with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenylcarbamates of Formula V can be prepared by the methods described, or modifications thereof known to those skilled in the art, in U.S. Pat. No. 4,443,243.

Alternatively, many of the compounds of Formula I can be prepared by the method described in Equation 2c.

Equation 2c

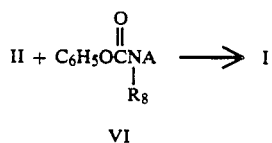

The reaction of Equation 2c can be carried out by contacting equimolar amounts of a sulfonamide of Formula II with a heterocyclic phenylcarbamate of Formula VI in the presence of a base such as 1,8-diazabicyclo[5.4.0]undec-7-ene (DBU), by methods analogous to those described in South African Patent Application 83/0441. The phenylcarbamates of Formula VI can be prepared by methods, or modifications thereof known to those skilled in the art, described in South African Patent Application 82/5671 and South African Patent Application 82/5045.

Sulfonamides of Formula II can be prepared from sulfonyl chlorides, by amination or other reactions known to one skilled in the art, which in turn are prepared by one of the reactions of Equations 3, 4 or 5.

Equation 3

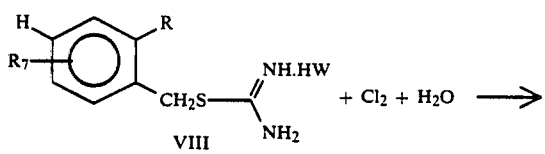

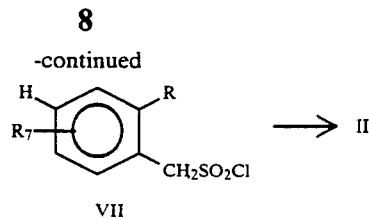

wherein:
R is $C(OR_3)R_2R_4$ or $C(OR_5)(OR_6)R_4$; W is Br or Cl; and $R_7$ is as previously defined.

Equation 4

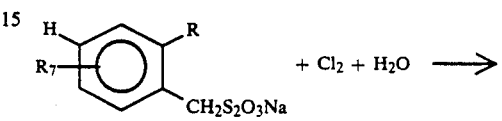

VII $\longrightarrow$ II wherein:
R is $C(OR_3)R_2R_4$ or $C(OR_5)(OR_6)R_4$; and $R_7$ is as previously defined.

Both reactions of Equations 3 and 4 involve oxidative chlorinations which can be carried out by using 3 to 6 equivalents of chlorine in a solvent such as water, wet acetic acid or wet propionic acid.

The thiouronium salts of Formula VIII can be prepared by the reaction of thiourea with a benzylic halide, usually in an alcohol solvent. The product can be isolated as a solid. The thiosulfate salts of Formula IX are prepared by the reaction of a benzylic halide and sodium thiosulfate in water at ambient, or above, temperatures. The product can usually be isolated directly as a solid, and is used without delay in the oxidative chlorination. The sulfonyl chlorides VII are converted to sulfonamides II, wherein R is $C(OR_3)R_2R_4$ or $C(OR_5)(OR_6)R_4$, by reaction with ammonia. This is a well known transformation.

Benzyl halides may be formed through a variety of methods described in the literature. Several are listed below.

BENZYLIC CHLORIDES (W=Cl)

Treatment of alkyl benzene derivatives with N-chlorosuccinimide, NCS, in a suitable solvent, such as carbon tetrachloride or dichloromethane, and catalyzed by light or a free radical initiator, such as azoisobutyronitrile or benzoyl peroxide, gives the benzylic chloride.

Treatment of a benzylic alcohol with thionyl chloride, either neat or in the presence of a base such as pyridine, gives the benzylic chloride. For typical examples, see H. Gilman and J. E. Kirby, *J. Am. Chem. Soc.*, 51, 3475 (1929) and M. S. Newman, *J. Am. Chem. Soc.*, 62, 2295 (1940).

BENZYLIC BROMIDES (W=Br)

Treatment of alkyl benzene derivatives with N-bromosuccinimide by a method analogous to the case of N-chlorosuccinimide gives the benzylic bromide. Benzylic alcohols in an inert solvent such as benzene or dichloromethane react with phosphorus tribromide to give benzylic bromides.

BENZYLIC IODIDES (W=I)

Treatment of a benzylic chloride or benzylic bromide with sodium iodide gives the benzylic iodide. The reaction, known as the Finkelstein reaction, works well in refluxing acetone.

Benzylic alcohols may be treated with iodine and phosphorus (red) or phosphorus (red) and phosphorus (yellow) to give the benzylic iodide.

Equation 5

$$\underset{X}{\text{H, R}_7\text{-C}_6\text{H}_3(\text{R})(\text{CH}_3)} \xrightarrow[\text{2) SO}_2, \text{NCS or SO}_2\text{Cl}_2]{\text{1) R'Li}} \underset{VII}{\text{H, R}_7\text{-C}_6\text{H}_3(\text{R})(\text{CH}_2\text{SO}_2\text{Cl})}$$

wherein:

R is $C(OH)R_1R_2$.

The toluenes of Formula X can be deprotonated with 2 equivalents of base (R'Li), such as n-butyllithium or LDA, as taught by H. Sano, H. Ohtsuka and T. Migita, *J. Am. Chem. Soc.*, 110 (1988), 2014–2015. The dianion can be quenched with sulfur dioxide followed by conversion of the sulfinate salt with N-chlorosuccinimide as taught in U.S. Pat. No. 4,481,029 (issued 11/6/84). The dianion can be converted directly to the sulfonyl chloride with sulfuryl chloride as taught by S. N. Bhattacharya et al., *J. Chem. Soc. C.*, (1968), 1265.

Conversion of the various R groups can be achieved for sulfonamides of Formula II by methods analogous to those shown for the sulfonylureas in the reactions of Equation 1a and 1b.

Toluene and benzylic alcohols are either known or easily prepared by one skilled in the art.

The dithiane sulfonyl isocyanates IV and their precursor sulfonamides of Formula II in Equation 2a are prepared from earlier ketone intermediates as described by D. Seebach and E. J. Corey, *J. Org. Chem.*, 40, (1975), 231, and U.S. Pat. No. 4,370,480 (issued 1/25/83).

The synthesis of heterocyclic amines have been reviewed in "The Chemistry of Heterocyclic Compounds", Vol. 16, Wiley-Interscience, N.Y. (1962). For a review of 2-aminopyrimidines see D. J. Brown in "The Pyrimidines", Vol. XVI of the above mentioned series. The pyrimidines where X is haloalkoxy can be prepared by the methods taught in U.S. Pat. No. 4,450,782. The 2-amino-1,3,5-triazines can be prepared according to the methods described by E. M. Smolin and L. Rapaport in "s-Triazines and Derivatives", Vol. XIII.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt of the resin and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following eight Examples.

EXAMPLE 1

α,2-Dimethylbenzenemethanol

In a dry flask under nitrogen atomosphere was suspended 3.25 g (0.086 mol) lithium aluminum hydride and 250 ml of dry diethyl ether. The suspension was cooled in an ice/water bath, then 24.5 g (0.184 mol) of 2-methylacetophenone was added dropwise. After 12 hours the excess hydride was decomposed with 100 ml of ethyl acetate. The reaction mixture was washed with ammonium chloride solution and water. The organic layer was dried (MgSO$_4$) and concentrated under reduced pressure to give 25.0 g of a clear oil.

PMR (CDCl$_3$, 90 MHz) δ 1.3 (d, CH$_3$, 3H), 2.3 (s, ArCH$_3$, 3H), 2.5 (d, OH, 1H), 5.0 (m, CH, 1H), 7.0–7.6 (m, ArH, 4H).

EXAMPLE 2

α,2-Dimethylbenzenemethanol, acetate 24.9 g (0.183 mol) of α,2-dimethylbenzenemethanol, 25.9 ml of acetic anhydride, 38 ml of triethylamine and 2.24 g of 4-dimethylaminopyridine was mixed under a nitrogen atmosphere, then allowed to stand at room temperature for 2 hours. The mixture was partitioned between 400 ml of diethyl ether and 300 ml of 2N HCl. The organic layer was washed with brine, bicarbonate solution, dried (MgSO$_4$) and concentrated under reduced pressure to give 34.4 9 of a brown oil. The oil was eluted with chloroform through a small plug of silica gel. The filtrate was concentrated under reduced pressure to give 32 g of a clear oil.

PMR (CDCl$_3$, 90 MHz) δ 1.5 (d, CH$_3$, 3H), 2.05 (s, CH$_3$C(O), 3H), 2.35 (s, ArCH$_3$, 3H), 6.1 (q, CH, 1H), 7.1–7.5 (m, ArH, 4H).

EXAMPLE 3

2-(Chloromethyl)-α-methylbenzenemethanol, acetate

A mixture of 11.71 g (0.065 mol) of the compound from Example 2, 9.65 g (0.072 mol) of N-chlorosuccinimide (NCS), 1 g of sodium bicarbonate and 250 ml of carbon tetrachloride was refluxed and illuminated with a sun lamp for 24 hours. Then the reaction mixture was filtered through sand and reilluminated in the presence of an additional 8 g NCS for 48 hours. The reaction mixture was filtered through a plug of silica gel and the filtrate was concentrated under reduced pressure to give 19 g of a brown oil which was eluted through a plug of silica gel with hexanes. The filtrate was concentrated to give 13.6 g as a light yellow oil.

PMR (CDCl$_3$, 90 MHz) δ 1.6 (d, CH$_3$, 3H), 2.07 (s, CH$_3$C(O), 3H), 4.59 and 4.97 (ABq, CH$_2$Cl, 2H), 6.1 (q, CH, 1H), 7.1–7.55 (m, ArH, 4H).

EXAMPLE 4

2-(1-Acetyloxyethyl)benzenemethanesulfonamide 2-(Chloroethyl)-α-methylbenzenemethanol, acetate, 15.81 g (0.074 mol) was dissolved in 200 ml of ethyl alcohol, then 5.8 g of thiourea was added and the reaction mixture was heated to reflux for 12 hours. The reaction mixture was concentrated under reduced pressure and the resulting oil was triturated twice with Et$_2$O/hexane (1:1), to give 22 g of gummy solid. The material was dissolved in 130 ml acetic acid and 5 ml of water, then cooled to 10° C. 15.64 ml of chlorine was added via a gas addition funnel and the reaction was allowed to warm to room temperature over 1 hour. The reaction was diluted with 300 ml ice/water. The milky solution was extracted with two portions of dichloromethane, which was washed successively with brine, bisulfite solution, brine and bicarbonate, then dried (MgSO$_4$). This solution was cooled to −78° C., then 6.7 ml of ammonia was added via a gas addition funnel and the mixture was stirred for 12 hours while warming to room temperature. The reaction mixture was washed with brine and 0.1N HCl, dried (MgSO$_4$), and concentrated under reduced pressure to give a solid. Trituration of the solid with diethyl ether/hexane (1:1) gave 3.75 g of a light yellow solid; m.p. 135°–140° C.

PMR (CDCl$_3$, 200 MHz) δ 1.50 (d, CH$_3$, 3H), 1.95 (s, CH$_3$C(O), 3H), 4.3 and 4.7 (ABq, CH$_2$SO$_2$, 2H), 6.05 (q, CH, 1H), 6.97 (bs, NH$_2$, 2H), 7.3–7.6 (m, ArH, 4H).

EXAMPLE 5

2-(1-Acetyloxyethyl)-N-[[(4,6-dimethoxy-1,3,5-triazin-2-yl)amino]carbonyl]benzenemethanesulfonamide To a suspension of 0.22 g (0.86 mmol) of the compound from Example 4 and 0.27 9 (0.9 mmol) of 4,6-dimethoxy-1,3,5-triazin-2-yl-carbamic acid, phenyl ester in 5 ml of dry acetonitrile was added 140 μl of 1,8-diazabicyclo[5.4.0]undec-7-ene (DBU). After one hour the reaction mixture was diluted with 10 ml of water, then acidified with 1N HCl. The resultant precipitate was collected, washed with water, then diethyl ether/hexane (1:1) to give 0.20 g of a white solid; m.p. 90°–95° C.

PMR (CCl$_3$, 200 MHz) δ 1.61 (d, CH$_3$, 3H), 1.98 (s, CH$_3$C(O), 3H), 3.96 (s, OCH$_3$, 6H), 4.8 and 5.4 (ABq, CH$_2$SO$_2$, 2H), 6.1 (q, CH, 1H), 7.15–7.55 (m, ArH, 4H), 8.4 and 11.8 (bs, NH, 2X1H).

EXAMPLE b 6

2-(1-Hydroxyethyl)benzenemethanesulfonamide

A mixture of 1.9 g (7.4 mmol) of 2-(1-acetyloxyethyl)-benzenemethanesulfonamide, 0.18 g of sodium methoxide (3.3 mmol) and 20 ml of methanol was stirred at room temperature for 2 days. The mixture was concentrated under reduced pressure and the residue was partitioned between ethyl acetate and 0.1N HCl. The organic layer was dried (MgSO$_4$) and concentrated to give 1.49 g of an oil which slowly solidified.

PMR (CCl$_3$, 90 MHz) δ 1.5 (d, CH$_3$, 3H), 2.5 (bs, OH, 1H), 4.45 (s, CH$_2$, 2H), 4.9–5.2 (bs/m, NH$_2$/CH, 3H), 7.2–7.6 (m, ArH, 4H).

EXAMPLE 7

N-[[(4,6-Dimethoxy-2-pyrimidinyl)amino]-carbonyl]-2-(1-hydroxyethyl)benzenemethanesulfonamide To a suspension of 0.5 g (2.3 mmol) of the compound from Example 6 and 0.74 g of 4,6-dimethoxy-2-pyrimidinylcarbamic acid, phenyl ester in 6 ml of acetonitrile was added 0.382 ml of DBU. The reaction mixture was stirred at room temperature for 1 hour, then diluted with 15 ml of water and acidified with 1N HCl. The resultant solid was collected, washed with water and diethyl ether/hexane (1:1) to give 0.51 g of a white solid; m.p. 147°–150° C.(d).

PMR (CDCl$_3$, 200 MHz) δ 1.54 (d, CH$_3$, 3H), 2.15 (bs, OH, 1H), 3.79 (s, OCH$_3$, 6H), 4.97 (s, CH$_2$SO$_2$, 2H), 5.3 (q, CH, 1H), 5.8 (s, pyrim-H, 1H), 7.2–7.6 (m, ArH+NH, 5H).

EXAMPLE 8

2-Acetyl-N-[[(4.6-dimethoxy-2-pyrimidinyl)-amino]carbonyl]benzenemethanesulfonamide A mixture of 0.40 g (1.04 mmol) of the compound from Example 7, 1.6 g of Celite®, 0.45 g of pyridinium chlorochromate (PCC) and 15 ml of dry dichloromethane was stirred for 5 hours under a nitrogen atmosphere. Then were added 1 ml of isopropyl alcohol, 1 g of charcoal and 2 g MgSO$_4$. The reaction mixture was eluted through a small plug of silica gel with 100 ml of ethyl acetate/hexane (1:1). The middle 80 ml of eluant was concentrated under reduced pressure to give 0.30 g of a light brown solid upon trituration with diethyl ether; m.p. 160°–163° C.(d).

PMR (CDCl$_3$, 200 MHz) δ 2.59 (s, CH$_3$C(O), 3H), 3.8 (s, OCH$_3$, 6H), 5.3 (s, CH$_2$SO$_2$, 2H), 5.74 (s, pryim-H, 1H), 7.2–7.6 (m/bs, ArH/NH, 4H), 7.7 (bm, ArH, 1H), 12.2 (bs, NH, 1H).

EXAMPLE 9

α-Ethyl-1,2-benzenedimethanol

To a cooled (~5° C.) suspension of sodium hydride (5.76 g), prewashed with dry hexanes, in 250 ml dry THF was added 18.7 g of 2-bromobenzylalcohol, portionwise. After evolution of gas had ceased the reaction mixture was cooled to −78° C., then 68.8 ml of 1.6M BuLi was added dropwise at a rate such that the temperature remained below −65° C. Then 14.28 ml of freshly distilled propionaldehyde was added, and the mixture was allowed to warm to room temperature. After 4 h brine was added to the reaction. The organic layer was separated, dried (MgSO$_4$), and concentrated to give 22.84 g yellow oil. The product was isolated by subjecting the oil to flash column chromatography, eluted with 25% EtOAc/hexanes up to 40% EtOAc/hexanes, to give 12.21 g of oil.

PMR (CDCl$_3$, 90 MHz) 0.9–1.1 (m, CH$_3$, 3H), 1.5–2.0 (m, CH$_2$, 2H), 3.25 (bs, OH, 2H), 4.5–4.9 (m, CH$_2$O and CHO, 3H), 7.2–7.4 (m, ArH, 4H).

EXAMPLE 10

2-[[(1,1-Dimethylethyl)dimethylsilyloxy]-methyl]-α-ethylbenzenemethanol

To a cooled (0° C.) solution of 8.44 g of α-ethyl-1,2-benzenedimethanol in 100 ml dry $CH_2Cl_2$ was added successively 7.77 ml of triethylamine, 8.81 g t-butyldimethylsilyl chloride and 0.31 g dimethylaminopyridine (DMAP). The reaction mixture was allowed to warm to room temperature, then it was worked up by adding 100 ml brine. The organic layer was separated and washed with bicarbonate, dried ($MgSO_4$) and filtered through a small plug of silica gel. The filtrate was concentrated under reduced pressure to give 10.63 g of an oil.

PMR ($CDCl_3$, 90 MHz) δ 0.15 (s, Si—$CH_3$, 6H), 0.9–1.2 (m, $CH_3$ and $SiC(CH_3)_3$, 12H), 1.5–2.1 (m, $CH_2$, 2H), 2.8 (d, OH, 1H), 4.9 (ABq, $CH_2O$, 2H), 7.2–7.7 (m, ArH, 4H).

EXAMPLE 11

2-[[(1,1-Dimethylethyl)dimethylsilyloxy]-methyl]-α-ethylbenzenemethanol, acetate A solution of 1.4 g of the product from Example 10, 0.91 ml of triethylamine, 0.61 ml acetic anhydride and 0.06 g DMAP was allowed to stand at room temperature overnight. The reaction was partitioned between 100 ml of ether and 75 ml of 1N HCl, the organic layer was dried ($MgSO_4$). The filtrate was subjected to flash column chromatography to give 1.45 g of product as an oil.

PMR ($CDCl_3$, 90 MHz) δ 0.2 (d, $SiCH_3$, 6H), 1.0 (m, $CH_3$ and t-butyl, 12H), 1.7–2.3 (m, $CH_2$ and $C(O)CH_3$, 5H), 4.7–5.2 (q, $CH_2O$, 2H), 5.9 (t, CHO, 1H), 7.2–7.6 (m, ArH, 4H).

EXAMPLE 12

2-[(Aminoiminomethylthio)methyl]-α-ethyl-benzenemethanol, acetate (ester), hydrochloride 7.04 ml of thionyl chloride was added to 15.55 g of 2-[[(1,1-dimethylethyl)dimethylsilyloxy]methyl]-α-ethyl-benzenemethanol, acetate, then heated to reflux under an $N_2$ atmosphere. After 3 h the reaction was concentrated under reduced pressure and the residue was subjected to flash column chromatography eluted with 10% ethyl acetate/hexanes, to give 7.66 g of a light yellow oil. This oil was dissolved in 200 ml of ethanol, followed by addition of 2.66 g thiourea. The mixture was heated to reflux for 1 h then concentrated under reduced pressure to give a yellow oil. Trituration of the oil with 1:1:1 acetone/diethyl ether/hexanes to give 9.60 g of a white solid, m.p. 151°–154° C.

PMR (Acetone-$d_6$, 90 MHz) δ 1.1 (t, $CH_3$, 3H), 1.8–2.2 (m, Acetone-$d_5$ and $C(O)CH_3$ and $CH_2$), 3.3 (s, $H_2O$), 5.0 (s, $CH_2S$, 2H), 6.0 (t, CH, 1H), 7.3–7.8 (m, ArH, 4H), 9.3 and 10.1 (bs, two $NH_24H$).

EXAMPLE 13

2-(1-Hydroxypropyl)benzenemethanesulfonamide

To a solution of 9.40 g of the compound from Example 12 in 2 ml water and 50 ml acetic acid, cooled to about 8° C., was added 7.76 ml $C_{12}$ dropwise via a gas addition funnel. The reaction was allowed to warm to room temperature, then 200 ml ice water was added, followed by 10 ml sodium bisulfite, 100 ml brine and 200 ml $CH_2Cl_2$. The organic layer was washed with brine, then bicarbonate solution, dried ($MgSO_4$) and filtered.

The filtrate was cooled to −70° C. under an $N_2$ atmosphere then 3.5 ml ammonia was added via a gas addition funnel. After 4 h the white precipitate was removed by filtration and the filtrate was dried ($MgSO_4$) and concentrated to give a white solid. Trituration with diethyl ether/hexanes (2:1) gave 2.28 gram of solid, m.p. 135°–145° C.

PMR ($CDCl_3$, 200 MHz) δ 0.98 (t, $CH_3$, 3H), 1.65–2.0 (m, $CH_2$, 2H), 2.07 (s, OAc, 3H), 4.6 (Abq, $CH_2SO_2$, 2H), 4.75 (bs, $NH_2$, 2H), 5.8 (m, CH, 1H), 7.2–7.6 (m, ArH, 4H).

1.68 g of this solid was suspended in 20 ml methanol, then added 0.13 g sodium methoxide. An additional 20 ml methanol was added and the solution was allowed to stand overnight. The reaction was concentrated under reduced pressure and the residue partitioned between slightly acidic brine and ethyl acetate. The organic layer was concentrated and the product was eluted through a silica gel column with 1:1 EtOAc/hexanes to give 0.93 g as a white solid, m.p. 101°–105° C.

PMR ($CDCl_3$, 90 MHz δ 0.95 (t, $CH_3$, 3H), 1.5–2.2 (m, $CH_2$, 2H), 3.05 (d, OH, 1H), 4.55 (s, $CH_2$, 2H), 4.7–5.1 (m, $NH_2$ and CH, 3H), 7.3–7.5 (m, ArH, 4H).

EXAMPLE 14

N-[[(4,6-Dimethoxy-2-pyrimidinyl)amino]carbonyl]-2-(1-hydroxypropyl)-benzenemethanesulfonamide To a solution of 0.46 g of the compound from Example 13 in 4 ml dry acetonitrile was added 0.61 g 4,6-dimethoxy-2-pyrimidinylcarbamic acid, phenyl ester followed by 330 μl of DBU. The reaction was worked up as in Example 7 to give 0.78 g white solid, m.p. 95°–98° C.

PMR (DMSO-$d_6$, 200 MHz) δ 0.89 (m, $CH_3$, 3H), 1.6 (m, $CH_2$, 2H), 3.78 (s, OMe, 6H), 4.8–4.95 (m, CH and $CH_2SO_2$, 3H), 5.96 (s, pyrm-H, 1H), 7.15–7.55 (m, ArH, 4H).

EXAMPLE 15

N-[[(4,6-Dimethoxy-2-pyrimidinyl)amino]carbonyl]-2-(1-oxopropyl)-benzenemethanesulfonamide A mixture of 0.30 g of the compound of Example 15 was dissolved in 20 ml dry $CH_2Cl_2$, then added 0.46 g Celite ® and 0.23 g PCC. The reaction was allowed to stir at room temperature overnight, then worked up as in Example 8 to give 0.22 g of product, m.p. 155°–158° C.

PMR ($CDCl_3$, 200 MHz) δ 1.19 (t, $CH_3$, 3H), 2.95 (q, $CH_2C(O)$, 2H), 3.79 (s, OMe, 6H), 5.3 (s, $CH_2SO_2$, 2H), 5.74 (s, pyrm-H, 1H), 7.3 (bs, NH, 1H), 7.40–7.7 (m, ArH, 4H), 12.2 (bs, NH, 1H).

Using the procedures from Equations 1 to 5 and Examples 1 to 15, the compounds of Tables I to IV can be prepared.

STRUCTURES FOR TABLES

TABLE I

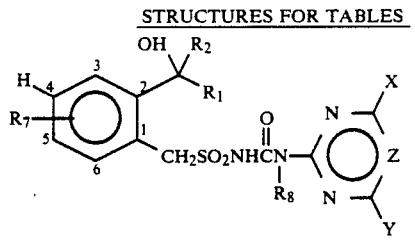

STRUCTURES FOR TABLES

TABLE II
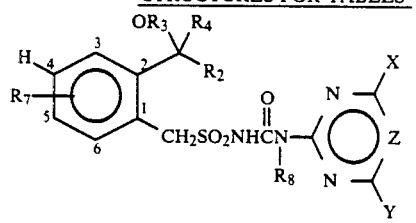

TABLE III
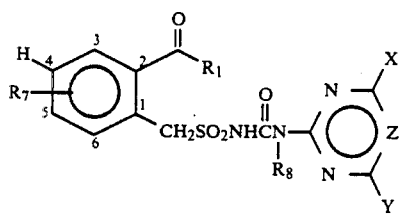

TABLE IV
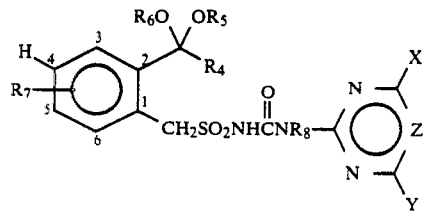

TABLE I

| R₁ | R₂ | R₇ | R₈ | X | Y | Z |
|---|---|---|---|---|---|---|
| CH₃ | H | H | H | CH₃ | CH₃ | CH |
| CH₃ | H | H | H | CH₃ | OCH₃ | CH |
| CH₃ | H | H | H | Cl | OCH₃ | CH |
| CH₃ | H | H | H | OCH₃ | OCH₃ | CH |
| CH₃ | H | H | H | CH₂OCH₃ | OCH₃ | CH |
| CH₃ | H | H | H | OCF₂H | OCH₃ | CH |
| CH₃ | H | H | H | OCH₃ | OCH₃ | N |
| CH₃ | H | H | H | OCH₂CH₃ | NHCH₃ | N |
| CH₃ | H | H | H | OCH₂CF₃ | NHCH₃ | N |
| CH₃ | H | H | H | OCH₂CF₃ | N(CH₃)₂ | N |
| CH₃ | H | H | H | OCH₂CH₃ | CH₂CH₃ | N |
| CH₃ | H | H | H | CH₃ | OCH₃ | N |
| CH₃ | H | 3-OCH₃ | H | OCH₃ | OCH₃ | CH |
| CH₃ | H | 3-Br | H | CH₃ | OCH₃ | N |
| CH₃ | H | 5-Cl | H | CH₃ | OCH₃ | CH |
| CH₃ | H | 5-OCH₃ | H | CH₃ | OCH₃ | CH |
| CH₃ | H | 6-F | H | CH₃ | OCH₃ | CH |
| CH₃ | H | 6-CF₃ | H | CH₃ | OCH₃ | CH |
| CH₃ | H | H | CH₃ | CH₃ | OCH₃ | CH |
| CH₃ | H | H | CH₃ | CH₃ | OCH₃ | N |
| CH₃ | H | H | CH₃ | OCH₃ | OCH₃ | N |
| CH₃ | CH₃ | H | H | OCH₃ | OCH₃ | CH |
| CH₃ | CH₃ | H | H | CH₃ | OCH₃ | N |
| CH₂CH₃ | H | H | H | CH₃ | CH₃ | CH |
| CH₂CH₃ | H | H | H | CH₃ | OCH₃ | CH |
| CH₂CH₃ | H | H | H | Cl | OCH₃ | CH |
| CH₂CH₃ | H | H | H | OCH₃ | OCH₃ | CH |
| CH₂CH₃ | H | H | H | CH₂OCH₃ | OCH₃ | CH |
| CH₂CH₃ | H | H | H | OCF₂H | OCH₃ | CH |
| CH₂CH₃ | H | H | H | OCH₃ | OCH₃ | N |
| CH₂CH₃ | H | H | H | OCH₂CH₃ | NHCH₃ | N |
| CH₂CH₃ | H | H | H | OCH₂CF₃ | NHCH₃ | N |
| CH₂CH₃ | H | H | H | OCH₂CF₃ | N(CH₃)₂ | N |
| CH₂CH₃ | H | H | H | OCH₂CH₃ | CH₂CH₃ | N |
| CH₂CH₃ | H | H | H | CH₃ | OCH₃ | N |
| CH₂CH₃ | H | 3-OCH₃ | H | OCH₃ | OCH₃ | CH |
| CH₂CH₃ | H | 3-Br | H | CH₃ | OCH₃ | N |
| CH₂CH₃ | H | 5-Cl | H | CH₃ | OCH₃ | CH |
| CH₂CH₃ | H | 5-OCH₃ | H | CH₃ | OCH₃ | CH |
| CH₂CH₃ | H | 6-F | H | CH₃ | OCH₃ | CH |
| CH₂CH₃ | H | 6-CF₃ | H | CH₃ | OCH₃ | CH |
| CH₂CH₃ | H | H | CH₃ | CH₃ | OCH₃ | CH |
| CH₂CH₃ | H | H | CH₃ | CH₃ | OCH₃ | N |
| CH₂CH₃ | H | H | CH₃ | OCH₃ | OCH₃ | N |
| CH₂CH₃ | CH₃ | H | H | OCH₃ | OCH₃ | CH |
| CH₂CH₃ | CH₃ | H | H | CH₃ | OCH₃ | N |
| CH₂CH₂CH₃ | H | H | H | CH₃ | CH₃ | CH |
| CH₂CH₂CH₃ | H | H | H | CH₃ | OCH₃ | CH |
| CH₂CH₂CH₃ | H | H | H | Cl | OCH₃ | CH |
| CH₂CH₂CH₃ | H | H | H | OCH₃ | OCH₃ | CH |
| CH₂CH₂CH₃ | H | H | H | CH₃ | OCH₃ | N |
| CH₂CH₂CH₃ | H | H | H | OCH₃ | OCH₃ | N |
| CH₂CH₂Cl | H | H | H | CH₃ | CH₃ | CH |
| CH₂CH₂Cl | H | H | H | CH₃ | OCH₃ | CH |
| CH₂CH₂Cl | H | H | H | Cl | OCH₃ | CH |
| CH₂CH₂Cl | H | H | H | OCH₃ | OCH₃ | CH |
| CH₂CH₂Cl | H | H | H | CH₃ | OCH₃ | N |
| CH₂CH₂Cl | H | H | H | OCH₃ | OCH₃ | N |
| CH₂CH₂Cl | H | H | CH₃ | OCH₃ | OCH₃ | CH |
| CF₃ | H | H | H | CH₃ | CH₃ | CH |
| CF₃ | H | H | H | CH₃ | OCH₃ | CH |
| CF₃ | H | H | H | Cl | OCH₃ | CH |
| CF₃ | H | H | H | OCH₃ | OCH₃ | CH |
| CF₃ | H | H | H | CH₃ | OCH₃ | N |
| CF₃ | H | H | H | OCH₃ | OCH₃ | N |
| CF₃ | CH₃ | H | H | OCH₃ | OCH₃ | CH |
| CH(CH₃)₂ | H | H | H | CH₃ | CH₃ | CH |
| CH(CH₃)₂ | H | H | H | OCH₃ | OCH₃ | CH |
| CH(CH₃)₂ | H | H | H | Cl | OCH₃ | CH |
| CH(CH₃)₂ | H | H | H | CH₃ | OCH₃ | N |
| CH(CH₃)₂ | H | H | H | OCH₃ | OCH₃ | N |
| CH₂CH₂OCH₃ | H | H | H | OCH₃ | OCH₃ | CH |
| CH₂CN | H | H | H | OCH₃ | OCH₃ | CH |
| CH₂SCH₃ | H | H | H | OCH₃ | OCH₃ | CH |
| CH₂CH₂CH₃ | H | 6-Cl | H | OCH₃ | OCH₃ | CH |

TABLE II

| R₂ | R₃ | R₄ | R₇ | R₈ | X | Y | Z |
|---|---|---|---|---|---|---|---|
| H | C(O)CH₃ | CH₃ | H | H | CH₃ | CH₃ | CH |
| H | C(O)CH₃ | CH₃ | H | H | CH₃ | OCH₃ | CH |
| H | C(O)CH₃ | CH₃ | H | H | Cl | OCH₃ | CH |
| H | C(O)CH₃ | CH₃ | H | H | OCH₃ | OCH₃ | CH |
| H | C(O)CH₃ | CH₃ | H | H | CH₂OCH₃ | OCH₃ | CH |
| H | C(O)CH₃ | CH₃ | H | H | OCF₂H | OCH₃ | CH |
| H | C(O)CH₃ | CH₃ | H | H | OCH₃ | OCH₃ | N |
| H | C(O)CH₃ | CH₃ | H | H | OCH₂CH₃ | NHCH₃ | N |
| H | C(O)CH₃ | CH₃ | H | H | OCH₂CF₃ | NHCH₃ | N |
| H | C(O)CH₃ | CH₃ | H | H | OCH₂CF₃ | N(CH₃)₂ | N |
| H | C(O)CH₃ | CH₃ | H | H | OCH₂CH₃ | CH₂CH₃ | N |
| H | C(O)CH₃ | CH₃ | H | H | CH₃ | OCH₃ | N |
| H | C(O)CH₃ | CH₃ | 3-OCH₃ | H | OCH₃ | OCH₃ | CH |
| H | C(O)CH₃ | CH₃ | 5-Cl | H | OCH₃ | OCH₃ | CH |
| H | C(O)CH₃ | CH₃ | 5-OCH₃ | H | OCH₃ | OCH₃ | CH |
| H | C(O)CH₃ | CH₃ | 6-F | H | OCH₃ | OCH₃ | CH |

TABLE II-continued

| R₂ | R₃ | R₄ | R₇ | R₈ | X | Y | Z |
|---|---|---|---|---|---|---|---|
| H | C(O)CH₃ | CH₃ | 6-CF₃ | H | OCH₃ | OCH₃ | CH |
| H | C(O)CH₃ | CH₃ | H | CH₃ | OCH₃ | OCH₃ | CH |
| H | C(O)CH₃ | CH₃ | H | CH₃ | CH₃ | OCH₃ | N |
| H | C(O)CH₃ | CH₃ | H | CH₃ | OCH₃ | OCH₃ | N |
| CH₃ | C(O)CH₃ | CH₃ | H | H | OCH₃ | OCH₃ | CH |
| CH₃ | C(O)CH₃ | CH₃ | H | H | CH₃ | OCH₃ | N |
| H | C(O)CH₂CH₃ | CH₃ | H | H | CH₃ | CH₃ | CH |
| H | C(O)CH₂CH₃ | CH₃ | H | H | CH₃ | OCH₃ | CH |
| H | C(O)CH₂CH₃ | CH₃ | H | H | Cl | OCH₃ | CH |
| H | C(O)CH₂CH₃ | CH₃ | H | H | OCH₃ | OCH₃ | CH |
| H | C(O)CH₂CH₃ | CH₃ | H | H | CH₃ | OCH₃ | N |
| H | C(O)CH₂CH₃ | CH₃ | H | H | OCH₃ | OCH₃ | N |
| H | C(O)CH₂CH₃ | CH₃ | 3-F | H | OCH₃ | OCH₃ | CH |
| H | C(O)CH₂CH₂CH₃ | CH₃ | H | H | OCH₃ | OCH₃ | CH |
| H | C(O)CH₂CH₂CH₃ | CH₃ | H | H | CH₃ | OCH₃ | N |
| H | C(O)cyclopropyl | CH₃ | H | H | OCH₃ | OCH₃ | CH |
| H | C(O)cyclopropyl | CH₃ | H | H | OCH₃ | OCH₃ | N |
| H | SO₂CH₃ | CH₃ | H | H | CH₃ | CH₃ | CH |
| H | SO₂CH₃ | CH₃ | H | H | CH₃ | OCH₃ | CH |
| H | SO₂CH₃ | CH₃ | H | H | Cl | OCH₃ | CH |
| H | SO₂CH₃ | CH₃ | H | H | OCH₃ | OCH₃ | CH |
| H | SO₂CH₃ | CH₃ | H | H | CH₃ | OCH₃ | N |
| H | SO₂CH₃ | CH₃ | H | H | OCH₃ | OCH₃ | N |
| H | SO₂CH₃ | CH₃ | H | CH₃ | OCH₃ | OCH₃ | CH |
| H | SO₂Et | CH₃ | H | CH₃ | CH₃ | OCH₃ | CH |
| H | SO₂Et | CH₃ | H | CH₃ | Cl | OCH₃ | CH |
| H | SO₂Et | CH₃ | H | CH₃ | OCH₃ | OCH₃ | CH |
| H | SO₂Et | CH₃ | H | CH₃ | CH₃ | OCH₃ | N |
| H | SO₂Et | CH₃ | H | CH₃ | OCH₃ | OCH₃ | N |
| H | C(O)C₆H₅ | CH₃ | H | CH₃ | OCH₃ | OCH₃ | CH |
| H | C(O)C₆H₅ | CH₃ | H | CH₃ | OCH₃ | OCH₃ | N |
| H | C(O)CH₃ | CH₂CH₃ | H | H | CH₃ | CH₃ | CH |
| H | C(O)CH₃ | CH₂CH₃ | H | H | CH₃ | OCH₃ | CH |
| H | C(O)CH₃ | CH₂CH₃ | H | H | Cl | OCH₃ | CH |
| H | C(O)CH₃ | CH₂CH₃ | H | H | OCH₃ | OCH₃ | CH |
| H | C(O)CH₃ | CH₂CH₃ | H | H | CH₂OCH₃ | OCH₃ | CH |
| H | C(O)CH₃ | CH₂CH₃ | H | H | OCF₂H | OCH₃ | CH |
| H | C(O)CH₃ | CH₂CH₃ | H | H | OCH₃ | OCH₃ | N |
| H | C(O)CH₃ | CH₂CH₃ | H | H | OCH₂CH₃ | NHCH₃ | N |
| H | C(O)CH₃ | CH₂CH₃ | H | H | OCH₂CF₃ | NHCH₃ | N |
| H | C(O)CH₃ | CH₂CH₃ | H | H | OCH₂CF₃ | N(CH₃)₂ | N |
| H | C(O)CH₃ | CH₂CH₃ | H | H | OCH₂CH₃ | CH₂CH₃ | N |
| H | C(O)CH₃ | CH₂CH₃ | H | H | CH₃ | OCH₃ | N |
| H | C(O)CH₃ | CH₂CH₃ | 3-OCH₃ | H | OCH₃ | OCH₃ | CH |
| H | C(O)CH₃ | CH₂CH₃ | 5-Cl | H | OCH₃ | OCH₃ | CH |
| H | C(O)CH₃ | CH₂CH₃ | 6-F | H | OCH₃ | OCH₃ | CH |
| H | C(O)CH₃ | CH₂CH₃ | 6-CF₃ | H | OCH₃ | OCH₃ | CH |
| H | C(O)CH₃ | CH₂CH₃ | H | CH₃ | OCH₃ | OCH₃ | CH |
| H | C(O)CH₃ | CH₂CH₃ | H | CH₃ | CH₃ | OCH₃ | N |
| H | C(O)CH₃ | CH₂CH₃ | H | CH₃ | OCH₃ | OCH₃ | N |
| CH₃ | C(O)CH₃ | CH₂CH₃ | H | H | OCH₃ | OCH₃ | CH |
| CH₃ | C(O)CH₃ | CH₂CH₃ | H | H | CH₃ | OCH₃ | N |
| H | C(O)CH₂CH₃ | CH₂CH₃ | H | H | OCH₃ | OCH₃ | CH |
| H | C(O)CH₂CH₃ | CH₂CH₃ | H | H | OCH₃ | OCH₃ | CH |
| H | C(O)CH₂CH₃ | CH₂CH₃ | H | CH₃ | OCH₃ | OCH₃ | CH |
| H | C(O)cyclopropyl | CH₂CH₃ | H | H | OCH₃ | OCH₃ | CH |
| H | C(O)cyclopropyl | CH₂CH₃ | H | H | OCH₃ | OCH₃ | N |
| H | C(O)C₆H₅ | CH₂CH₃ | H | H | OCH₃ | OCH₃ | CH |
| H | C(O)C₆H₅ | CH₂CH₃ | H | H | OCH₃ | OCH₃ | N |
| H | SO₂CH₂CH₃ | CH₂CH₃ | H | H | OCH₃ | OCH₃ | CH |
| H | SO₂CH₂CH₂CH₃ | CH₂CH₃ | H | H | OCH₃ | OCH₃ | CH |
| H | SO₂CH₃ | CH₂CH₃ | H | H | CH₃ | CH₃ | CH |
| H | SO₂CH₃ | CH₂CH₃ | H | H | CH₃ | OCH₃ | CH |
| H | SO₂CH₃ | CH₂CH₃ | H | H | Cl | OCH₃ | CH |
| H | SO₂CH₃ | CH₂CH₃ | H | H | OCH₃ | OCH₃ | CH |
| H | SO₂CH₃ | CH₂CH₃ | H | H | CH₃ | OCH₃ | N |
| H | SO₂CH₃ | CH₂CH₃ | H | H | OCH₃ | OCH₃ | N |
| H | C(O)CH₃ | CH₂CH₂CH₃ | H | H | CH₃ | CH₃ | CH |
| H | C(O)CH₃ | CH₂CH₂CH₃ | H | H | CH₃ | OCH₃ | CH |
| H | C(O)CH₃ | CH₂CH₂CH₃ | H | H | Cl | OCH₃ | CH |
| H | C(O)CH₃ | CH₂CH₂CH₃ | H | H | OCH₃ | OCH₃ | CH |
| H | C(O)CH₃ | CH₂CH₂CH₃ | H | H | CH₃ | OCH₃ | N |
| H | C(O)CH₃ | CH₂CH₂CH₃ | H | H | OCH₃ | OCH₃ | N |
| H | C(O)CH₃ | CH₂CH₂Cl | H | H | CH₃ | CH₃ | CH |
| H | C(O)CH₃ | CH₂CH₂Cl | H | H | CH₃ | OCH₃ | CH |
| H | C(O)CH₃ | CH₂CH₂Cl | H | H | Cl | OCH₃ | CH |
| H | C(O)CH₃ | CH₂CH₂Cl | H | H | OCH₃ | OCH₃ | CH |
| H | C(O)CH₃ | CH₂CH₂Cl | H | H | CH₃ | OCH₃ | N |
| H | C(O)CH₃ | CH₂CH₂Cl | H | H | OCH₃ | OCH₂ | N |
| H | C(O)CH₃ | CF₃ | H | CH₃ | OCH₃ | OCH₃ | CH |
| H | C(O)CH₃ | CF₃ | H | CH₃ | CH₃ | OCH₃ | CH |

TABLE II-continued

| $R_2$ | $R_3$ | $R_4$ | $R_7$ | $R_8$ | X | Y | Z |
|---|---|---|---|---|---|---|---|
| H | C(O)CH$_3$ | CF$_3$ | H | CH$_3$ | Cl | OCH$_3$ | CH |
| H | C(O)CH$_3$ | CF$_3$ | H | CH$_3$ | OCH$_3$ | OCH$_3$ | CH |
| H | C(O)CH$_3$ | CF$_3$ | H | CH$_3$ | CH$_3$ | OCH$_3$ | N |
| H | C(O)CH$_3$ | CF$_3$ | H | CH$_3$ | OCH$_3$ | OCH$_3$ | N |
| CH$_3$ | C(O)CH$_3$ | CF$_3$ | H | CH$_3$ | OCH$_3$ | OCH$_3$ | CH |
| H | C(O)CH$_3$ | CH(CH$_3$)$_2$ | H | CH$_3$ | CH$_3$ | OCH$_3$ | CH |
| H | C(O)CH$_3$ | CH(CH$_3$)$_2$ | H | CH$_3$ | OCH$_3$ | OCH$_3$ | CH |
| H | C(O)CH$_3$ | CH(CH$_3$)$_2$ | H | CH$_3$ | Cl | OCH$_3$ | CH |
| H | C(O)CH$_3$ | CH(CH$_3$)$_2$ | H | CH$_3$ | CH$_3$ | OCH$_3$ | N |
| H | C(O)CH$_3$ | CH(CH$_3$)$_2$ | H | CH$_3$ | OCH$_3$ | OCH$_3$ | N |
| H | C(O)CH$_3$ | CH$_2$CH$_2$OCH$_3$ | H | CH$_3$ | OCH$_3$ | OCH$_3$ | CH |
| H | C(O)CH$_3$ | CH$_2$CN | H | CH$_3$ | OCH$_3$ | OCH$_3$ | CH |
| H | C(O)CH$_3$ | CH$_2$SCH$_3$ | H | CH$_3$ | OCH$_3$ | OCH$_3$ | CH |
| H | C(O)CH$_3$ | CH$_2$CH$_2$CH$_3$ | 6-F | CH$_3$ | OCH$_3$ | OCH$_3$ | CH |

TABLE III

| $R_1$ | $R_7$ | $R_8$ | X | Y | Z |
|---|---|---|---|---|---|
| CH$_3$ | H | H | CH$_3$ | CH$_3$ | CH |
| CH$_3$ | H | H | CH$_3$ | OCH$_3$ | CH |
| CH$_3$ | H | H | Cl | OCH$_3$ | CH |
| CH$_3$ | H | H | OCH$_3$ | OCH$_3$ | CH |
| CH$_3$ | H | H | CH$_2$OCH$_3$ | OCH$_3$ | CH |
| CH$_3$ | H | H | OCF$_2$H | OCH$_3$ | CH |
| CH$_3$ | H | H | OCH$_3$ | OCH$_3$ | N |
| CH$_3$ | H | H | OCH$_2$CH$_3$ | NHCH$_3$ | N |
| CH$_3$ | H | H | OCH$_2$CF$_3$ | NHCH$_3$ | N |
| CH$_3$ | H | H | OCH$_2$CF$_3$ | N(CH$_3$)$_2$ | N |
| CH$_3$ | H | H | OCH$_2$CH$_3$ | CH$_2$CH$_3$ | N |
| CH$_3$ | H | H | CH$_3$ | OCH$_3$ | N |
| CH$_3$ | 3-OCH$_3$ | H | OCH$_3$ | OCH$_3$ | CH |
| CH$_3$ | 3-Br | H | CH$_3$ | OCH$_3$ | N |
| CH$_3$ | 5-Cl | H | CH$_3$ | OCH$_3$ | CH |
| CH$_3$ | 5-OCH$_3$ | H | CH$_3$ | OCH$_3$ | CH |
| CH$_3$ | 6-F | H | CH$_3$ | OCH$_3$ | CH |
| CH$_3$ | 6-CF$_3$ | H | CH$_3$ | OCH$_3$ | CH |
| CH$_3$ | H | CH$_3$ | OCH$_3$ | OCH$_3$ | CH |
| CH$_3$ | H | CH$_3$ | OCH$_3$ | OCH$_3$ | N |
| CH$_3$ | H | CH$_3$ | OCH$_3$ | OCH$_3$ | N |
| CH$_2$CH$_3$ | H | H | CH$_3$ | CH$_3$ | CH |
| CH$_2$CH$_3$ | H | H | CH$_3$ | OCH$_3$ | CH |
| CH$_2$CH$_3$ | H | H | Cl | OCH$_3$ | CH |
| CH$_2$CH$_3$ | H | H | OCH$_3$ | OCH$_3$ | CH |
| CH$_2$CH$_3$ | H | H | CH$_2$OCH$_3$ | OCH$_3$ | CH |
| CH$_2$CH$_3$ | H | H | OCF$_2$H | OCH$_3$ | CH |
| CH$_2$CH$_3$ | H | H | OCH$_3$ | OCH$_3$ | N |
| CH$_2$CH$_3$ | H | H | OCH$_2$CH$_3$ | NHCH$_3$ | N |
| CH$_2$CH$_3$ | H | H | OCH$_2$CF$_3$ | NHCH$_3$ | N |
| CH$_2$CH$_3$ | H | H | OCH$_2$CF$_3$ | N(CH$_3$)$_2$ | N |
| CH$_2$CH$_3$ | H | H | OCH$_2$CH$_3$ | CH$_2$CH$_3$ | N |
| CH$_2$CH$_3$ | H | H | CH$_3$ | OCH$_3$ | N |
| CH$_2$CH$_3$ | 3-OCH$_3$ | H | OCH$_3$ | OCH$_3$ | CH |
| CH$_2$CH$_3$ | 3-Br | H | CH$_3$ | OCH$_3$ | N |
| CH$_2$CH$_3$ | 5-Cl | H | CH$_3$ | OCH$_3$ | CH |
| CH$_2$CH$_3$ | 5-OCH$_3$ | H | CH$_3$ | OCH$_3$ | CH |
| CH$_2$CH$_3$ | 6-F | H | CH$_3$ | OCH$_3$ | CH |
| CH$_2$CH$_3$ | 6-CF$_3$ | H | CH$_3$ | OCH$_3$ | CH |
| CH$_2$CH$_3$ | H | CH$_3$ | CH$_3$ | OCH$_3$ | CH |
| CH$_2$CH$_3$ | H | CH$_3$ | CH$_3$ | OCH$_3$ | N |
| CH$_2$CH$_3$ | H | CH$_3$ | OCH$_3$ | OCH$_3$ | N |
| CH$_2$CH$_2$CH$_3$ | H | H | CH$_3$ | CH$_3$ | CH |
| CH$_2$CH$_2$CH$_3$ | H | H | OCH$_3$ | OCH$_3$ | CH |
| CH$_2$CH$_2$CH$_3$ | H | H | Cl | OCH$_3$ | CH |
| CH$_2$CH$_2$CH$_3$ | H | H | OCH$_3$ | OCH$_3$ | CH |
| CH$_2$CH$_2$CH$_3$ | H | H | CH$_3$ | OCH$_3$ | N |
| CH$_2$CH$_2$CH$_3$ | H | H | OCH$_3$ | OCH$_3$ | N |
| CH(CH$_3$)$_2$ | H | H | CH$_3$ | CH$_3$ | CH |
| CH(CH$_3$)$_2$ | H | H | CH$_3$ | OCH$_3$ | CH |
| CH(CH$_3$)$_2$ | H | H | Cl | OCH$_3$ | CH |
| CH(CH$_3$)$_2$ | H | H | OCH$_3$ | OCH$_3$ | CH |
| CH(CH$_3$)$_2$ | H | H | CH$_3$ | OCH$_3$ | N |
| CH(CH$_3$)$_2$ | H | H | OCH$_3$ | OCH$_3$ | N |
| CH$_2$OCH$_3$ | H | H | CH$_3$ | CH$_3$ | CH |
| CH$_2$OCH$_3$ | H | H | CH$_3$ | OCH$_3$ | CH |
| CH$_2$OCH$_3$ | H | H | Cl | OCH$_3$ | CH |
| CH$_2$OCH$_3$ | H | H | OCH$_3$ | OCH$_3$ | CH |
| CH$_2$OCH$_3$ | H | H | CH$_3$ | OCH$_3$ | N |
| CH$_2$OCH$_3$ | H | H | OCH$_3$ | OCH$_3$ | N |
| CH$_2$CH$_2$Cl | H | H | CH$_3$ | CH$_3$ | CH |
| CH$_2$CH$_2$Cl | H | H | CH$_3$ | OCH$_3$ | CH |
| CH$_2$CH$_2$Cl | H | H | Cl | OCH$_3$ | CH |
| CH$_2$CH$_2$Cl | H | H | OCH$_3$ | OCH$_3$ | CH |
| CH$_2$CH$_2$Cl | H | H | CH$_3$ | OCH$_3$ | N |
| CH$_2$CH$_2$Cl | H | H | OCH$_3$ | OCH$_3$ | N |
| CH$_2$CH$_2$OCH$_3$ | H | H | OCH$_3$ | OCH$_3$ | CH |
| CF$_3$ | H | H | OCH$_3$ | OCH$_3$ | CH |
| CH$_2$SCH$_3$ | H | H | OCH$_3$ | OCH$_3$ | CH |
| CH$_2$CN | H | H | OCH$_3$ | OCH$_3$ | CH |

TABLE IV

| $R_4$ | $R_5$ | $R_6$ | $R_7$ | $R_8$ | X | Y | Z |
|---|---|---|---|---|---|---|---|
| H | CH$_3$ | CH$_3$ | H | H | CH$_3$ | CH$_3$ | CH |
| H | CH$_3$ | CH$_3$ | H | H | CH$_3$ | OCH$_3$ | CH |
| H | CH$_3$ | CH$_3$ | H | H | Cl | OCH$_3$ | CH |
| H | CH$_3$ | CH$_3$ | H | H | OCH$_3$ | OCH$_3$ | CH |
| H | CH$_3$ | CH$_3$ | H | H | CH$_3$ | OCH$_3$ | N |
| H | CH$_3$ | CH$_3$ | H | H | OCH$_3$ | OCH$_3$ | N |
| CH$_3$ | CH$_3$ | CH$_3$ | H | H | CH$_3$ | CH$_3$ | CH |
| CH$_3$ | CH$_3$ | CH$_3$ | H | H | CH$_3$ | OCH$_3$ | CH |
| CH$_3$ | CH$_3$ | CH$_3$ | H | H | Cl | OCH$_3$ | CH |
| CH$_3$ | CH$_3$ | CH$_3$ | H | H | OCH$_3$ | OCH$_3$ | CH |
| CH$_3$ | CH$_3$ | CH$_3$ | H | H | CH$_3$ | OCH$_3$ | N |
| CH$_3$ | CH$_3$ | CH$_3$ | H | H | OCH$_3$ | OCH$_3$ | N |
| CH$_3$ | CH$_2$CH$_3$ | CH$_2$CH$_3$ | H | H | CH$_3$ | CH$_3$ | CH |
| CH$_3$ | CH$_2$CH$_3$ | CH$_2$CH$_3$ | H | H | CH$_3$ | OCH$_3$ | CH |
| CH$_3$ | CH$_2$CH$_3$ | CH$_2$CH$_3$ | H | H | Cl | OCH$_3$ | CH |
| CH$_3$ | CH$_2$CH$_3$ | CH$_2$CH$_3$ | H | H | OCH$_3$ | OCH$_3$ | CH |
| CH$_3$ | CH$_2$CH$_3$ | CH$_2$CH$_3$ | H | H | CH$_3$ | OCH$_3$ | N |
| CH$_3$ | CH$_2$CH$_3$ | CH$_2$CH$_3$ | H | H | OCH$_3$ | OCH$_3$ | N |
| CH$_2$CH$_3$ | CH$_3$ | CH$_3$ | H | H | CH$_3$ | CH$_3$ | CH |
| CH$_2$CH$_3$ | CH$_3$ | CH$_3$ | H | H | CH$_3$ | OCH$_3$ | CH |
| CH$_2$CH$_3$ | CH$_3$ | CH$_3$ | H | H | Cl | OCH$_3$ | CH |
| CH$_2$CH$_3$ | CH$_3$ | CH$_3$ | H | H | OCH$_3$ | OCH$_3$ | CH |
| CH$_2$CH$_3$ | CH$_3$ | CH$_3$ | H | H | CH$_3$ | OCH$_3$ | N |
| CH$_2$CH$_3$ | CH$_3$ | CH$_3$ | H | H | OCH$_3$ | OCH$_3$ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 5

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

In the following examples, all parts are by weight unless otherwise indicated.

EXAMPLE 16

Wettable Powder

| | |
|---|---|
| 2-[1-(Acetyloxy)ethyl]-N-[[(4,6-dimethoxy-2-pyrimidinyl)amino]carbonyl]benzenemethane-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 50 microns in diameter. The product is reblended before packaging.

EXAMPLE 17

Granule

| | |
|---|---|
| Wettable Powder of Example 16 | 5% |
| attapulgite granules (U.S.S. 20-40 mesh; 0.84-0.42 mm) | 95% |

A slurry of wettable powder containing 25% solids is sprayed on the surface of attapulgite granules in a double-cone blender. The granules are dried and packaged.

EXAMPLE 18

Extruded Pellet

| | |
|---|---|
| 2-Acetyl-N-[[(4,6-dimethoxy-2-pyrimidinyl)amino]carbonyl]benzenemethanesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

Low Strength Granule

| | |
|---|---|
| N-[[(4,6-dimethoxy-2-pyrimidinyl)amino]carbonyl]-2-(1-hydroxyethyl)benzenemethanesulfonamide | 1% |
| N,N-dimethylformamide | 9% |
| attapulgite granules (U.S.S. 20-40 sieve, 0.42 to 0.84 mm) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 20

Aqueous Suspension

| | |
|---|---|
| 2-[1-(Acetyloxy)ethyl]-N-[[(4,6-dimethoxy-2-pyrimidinyl)amino]carbonyl]benzenemethane-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 21

Oil Suspension

| | |
|---|---|
| 2-Acetyl-N-[[(4,6-dimethoxy-2-pyrimidinyl)amino]-carbonyl]benzenemethanesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

Granule

| | |
|---|---|
| N-[[(4,6-dimethoxy-2-pyrimidinyl)amino]carbonyl]-benzenemethanesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh (149 microns) screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 23

High Strength Concentrate

| | |
|---|---|
| 2-[1-(Acetyloxy)ethyl]-N-[[(4,6-dimethoxy-2-pyrimidinyl)amino]carbonyl]benzenemethane-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 24

Wettable Powder

| | |
|---|---|
| 2-Acetyl-N-[[(4,6-dimethoxy-2-pyrimidinyl)amino]-carbonyl]benzenemethanesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 25

Wettable Powder

| | |
|---|---|
| N-[[(4,6-dimethoxy-2-pyrimidinyl)amino]carbonyl]-2-(1-hydroxyethyl)benzenemethanesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 26

Dust

| | |
|---|---|
| 2-[1-(Acetyloxy)ethyl]-N-[[(4,6-dimethoxy-2-pyrimidinyl)amino]carbonyl]benzenemethane-sulfonamide | 10% |
| attapulgite | 10% |
| talc | 80% |

The active ingredient is blended with attapulgite and then passed through a hammer-mill to produce particles substantially all below 200 microns. The ground concentrate is then blended with powdered pyrophyllite until homogeneous.

EXAMPLE 27

Solution

| | |
|---|---|
| 2-Acetyl-N-[[(4,6-dimethoxy-2-pyrimidinyl)amino]-carbonyl]benzenemethanesulfonamide, sodium salt | 5% |
| water | 95% |

The salt is added directly to the water with stirring to produce the solution, which may then be packaged for use.

EXAMPLE 28

Solution

| | |
|---|---|
| 2-[1-(Acetyloxy)ethyl]-N-[[(4,6-dimethoxy-2-pyrimidinyl)amino]carbonyl]benzenemethane-sulfonamide, sodium salt | 5% |
| water | 95% |

The salt is added directly to the water with stirring to produce the solution, which may then be packaged for use.

Utility

Test results indicate that compounds of the present invention are highly active preemergent and/or postemergent herbicides or plant growth regulants. These compounds have utility for selected grass and broadleaf weed control in dry-land and paddy rice (*Oryza sativa*); examples of which include, but are not limited, Indica and Japonica varieties of the crop. Many of the compounds of this invention are particularly useful for the control of selected grass and broadleaf weeds in paddy rice. These compounds are especially useful for the control of selected grass and broadleaf weeds such as arrowhead (Sagittaria spp.), barnyardgrass (*Echinochloa*

*crus-galli*), bulrush (*Scirpus* spp.), duck salad (*Heteranthera* spp.), and sedge (*Cyperus* spp.) in transplanted paddy rice. Several compounds of this invention are useful for control of selected broadleaf weeds such as catchweed bedstraw (*Galium* spp. , field pennycress (*Thlaspi arvense*), Russian thistle (*Salsola kali*), and scentless chamomile (*Matricaria inodora*) in cereal crops such as wheat (*Triticum aestivum*) and barley (*Hordeum vulgare*). These compounds also have utility for broad-spectrum pre- and/or postemergence weed control in areas where control of all vegetation is desired such as around storage tanks, parking lots, drive-in theaters, billboards, highways, railroad structures, and in fallow areas. Alternatively, these compounds are useful to modify plant growth and as citrus abscission harvest aids.

Effective amounts of the compounds of this invention are determined by a number of factors. These factors include: formulation selected, method of application, amount of vegetation present, growing conditions, etc. In general terms, effective amounts of the subject compounds are applied at rates from 0.001 to 20 kg/ha, with a preferred rate range of from 0.004 to 0.25 kg/ha. One skilled in the art can easily determine application rates necessary for the desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl-3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |

-continued

| Common Name | Chemical Name |
|---|---|
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142, 464 | 3-(4,6-dimethoxy-1,3,5-triazin-2-yl)-1-[2-(2-methoxyethoxy)phenyl-sulfonyl]urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]-amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitro-phenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzene-sulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7 oxabicyclo-[2.2.1]heptane |
| clethodim | (E,E)-(±)-2-[1-[[(3 chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy]-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzene-dicarboxylate |
| desmediphan | ethyl [3-[[(phenylamino)carbonyl]oxy]-phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]-propanoic acid, methyl ester |
| diethatyl | N-(chloroacetyl)-N-(2,6-diethylphenyl)-glycine |
| difenzoquat | 1,2-dimethyl-3,5-diphenyl-1H-pyrazolium |
| dimepiperate | S-1-methyl-1-phenylethylpiperidine-1-carbothioate |

-continued

| Common Name | Chemical Name |
|---|---|
| dinitramine | N³,N³-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb (SC2957) | S-benzyl-N-ethyl-N-(1,2-dimethyl)propyl)thiolcarbamate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazin-2-yl)-N-methylamino]carbonyl]amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |

-continued

| Common Name | Chemical Name |
|---|---|
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothionate |
| mecoprop | (±)-2-(4-chloro-2-methylphenoxy)propanoic acid |
| mefenacet | 2-(2-benzothiazolyloxy-N-methyl-N-phenylacetamide |
| mefluidide | N-[2,4-dimethyl-5-[[(trifluoromethyl)sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,-4α, 5α, 7α, 7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzeneamine |

| Common Name | Chemical Name |
|---|---|
| perfluidone | 1,1,1-trifluoro-N-[2-methyl-4-(phenyl-sulfonyl)phenyl]methanesulfonamide |
| phenmedipham | 3-[methoxycarbonyl)amino]phenyl (3-methylphenyl)carbamate |
| picloram | 4-amino-3,5,6-trichloro-2-pyridine-carboxylic acid |
| PPG-1013 | 5-[2-chloro-4-(trifluoromethyl)-phenoxy]-2-nitroacetophenone oxime-O-acetic acid, methyl ester |
| pretilachlor | α-chloro-2,6-diethyl-N-(2-propoxy-ethyl)acetanilide |
| procyazine | 2-[[4-chloro-6-(cyclopropylamino)-1,3,5-triazine-2-yl]amino]-2-methylpropane-nitrile |
| profluralin | N-(cyclopropylmethyl)-2,6-dinitro-N-propyl-4-(trifluoromethyl)benzeneamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propyn-yl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N[[4-(dipropylamino)-3,5-dinitro-phenyl]sulfonyl]-S,S-dimethylsulfil-imine |
| prynachlor | 2-chloro-N-(1-methyl-2-propynyl)acet-anilide |
| pyrazolate | 4-(2,4-dichlorobenzoyl)-1,3-dimethyl-pyrazol-5-yl-p-toluenesulphonate |
| pyrazon | 5-amino-4-chloro-2-phenyl-3(2H)-pyridazinone |
| pyrazosulfuron ethyl | ethyl S-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethyl-thio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(α,α-dimethylbenzyl)-3-(4-methyl-phenyl)urea |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadi-azol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthyl-azine | 2-(tert-butylamino)-4-chloro-6-(ethyl-amino)-s-triazine |
| terbutol | 2,6-di-tert-butyl-p-tolyl methylcar-bamate |
| terbutryn | N-(1,1-dimethylethyl)-N'-ethyl-6-(methylthio)-1,3,5-triazine-2,4-diamine |
| thiobencarb | S-[(4-chlorophenyl)methyl] diethylcar-bamothioate |
| triallate | S-(2,3,3-trichloro-2-propenyl) bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(tri-fluoromethyl)benzenamine |
| trimeturon | 1-(p-chlorophenyl)-2,3,3-trimethylpseu-dourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

COMPOUNDS

Structure: phenyl ring with CHR$_1$(OH) substituent and CH$_2$S(O)$_2$NHC(O)NH- linked to a 6-membered N,N-heterocycle with substituents X, Y, Z.

| CMPD | R$_1$ | X | Y | Z | m.p. (°C.) |
|---|---|---|---|---|---|
| 1 | CH$_3$ | OCH$_3$ | OCH$_3$ | CH | 147–150 (d) |
| 2 | CH$_3$ | CH$_3$ | OCH$_3$ | CH | 149–152 (d) |
| 3 | CH$_3$ | CH$_3$ | CH$_3$ | CH | oil$^{(a)}$ |
| 4 | CH$_3$ | OCH$_3$ | OCH$_3$ | N | oil$^{(b)}$ |
| 5 | CH$_3$ | CH$_3$ | OCH$_3$ | N | oil$^{(c)}$ |
| 6 | CH$_2$CH$_2$Cl | OCH$_3$ | OCH$_3$ | CH | 90–95 |
| 7 | CH$_2$CH$_2$Cl | CH$_3$ | OCH$_3$ | N | 75–78 |

Structure: phenyl ring with CHR$_4$(OC(O)CH$_3$) substituent and CH$_2$S(O)$_2$NHC(O)NH- linked to heterocycle.

| CMPD | R$_4$ | X | Y | Z | m.p. (°C.) |
|---|---|---|---|---|---|
| 8 | CH$_3$ | CH$_3$ | CH$_3$ | CH | 125–130 |
| 9 | CH$_3$ | OCH$_3$ | OCH$_3$ | CH | 128–131 |
| 10 | CH$_3$ | OCH$_3$ | OCH$_3$ | N | 90–95 |
| 11 | CH$_3$ | CH$_3$ | OCH$_3$ | CH | 65–70 |
| 12 | CH$_2$CH$_2$Cl | OCH$_3$ | OCH$_3$ | CH | 138–140 |
| 13 | CH$_2$CH$_2$Cl | OCH$_3$ | OCH$_3$ | N | 65–70 (d) |
| 14 | CH$_2$CH$_2$Cl | CH$_3$ | OCH$_3$ | N | 63–68 (d) |

Structure: phenyl ring with C(O)R$_1$ substituent and CH$_2$S(O)$_2$NHC(O)NH- linked to heterocycle.

| CMPD | R$_1$ | X | Y | Z | m.p. (°C.) |
|---|---|---|---|---|---|
| 15 | CH$_3$ | OCH$_3$ | OCH$_3$ | CH | 160–163 (d) |
| 16 | CH$_3$ | CH$_3$ | OCH$_3$ | CH | 151–154 |
| 17 | CH$_2$CH$_2$Cl | OCH$_3$ | OCH$_3$ | CH | 145–150 |
| 18 | CH$_3$ | CH$_3$ | OCH$_3$ | N | 140–144 |
| 19 | CH$_2$CH$_2$Cl | CH$_3$ | OCH$_3$ | N | 85–89 |

-continued
COMPOUNDS

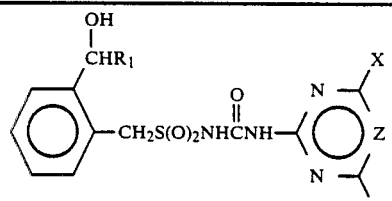

| CMPD | R₁ | X | Y | Z | m.p. (°C.) |
|---|---|---|---|---|---|
| 20 | CH₂CH₃ | OCH₃ | OCH₃ | CH | 95-98 |
| 21 | CH₂CH₃ | CH₃ | OCH₃ | CH | 100-104 |

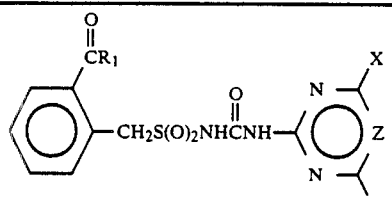

| CMPD | R₁ | X | Y | Z | m.p. (°C.) |
|---|---|---|---|---|---|
| 22 | CH₂CH₃ | OCH₃ | OCH₃ | CH | 155-158 |
| 23 | CH₂CH₃ | CH₃ | OCH₃ | CH | 150-155 |

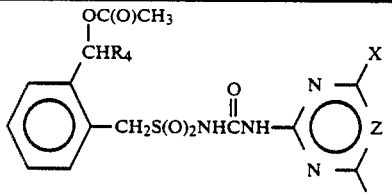

| CMPD | R₄ | X | Y | Z | m.p. (°C.) |
|---|---|---|---|---|---|
| 24 | CH₂CH₃ | OCH₃ | OCH₃ | CH | 170-172 |
| 25 | CH₂CH₃ | CH₃ | OCH₃ | CH | oil$^{(d)}$ |
| 26 | CH₂CH₃ | OCH₃ | OCH₃ | N | 135-140 |

-continued
COMPOUNDS

| | | | | | |
|---|---|---|---|---|---|
| 27 | CH₂CH₃ | CH₃ | OCH₃ | N | 98-100 |

Notes:
$^{(a)}$PMR(CDCl₃, 200 MHz): δ 1.55(d, CH₃, 3H), 2.1(s, OH, 1H), 2.4(s, CH₃, 6H), 5.0(s, CH₂SO₂, 2H), 5.36(q, CHO, 1H), 6.75(s, pyrm-H, 1H), 7.2-7.6(m, ArH and NH, 5H) and 8.7(bs, NH, 1H).

$^{(b)}$PMR(CDCl₃, 200 MHz): δ 1.53(d, CH₃, 3H), 2.1(s, OH, 1H), 3.96(s, OMe, 6H), 4.97(s, CH₂SO₂, 2H), 5.3(q, CHO, 1H), 7.2-7.6(m, ArH and NH, 5H) and 8.6(bs, NH, 1H).

$^{(c)}$PMR(CDCl₃, 200 MHz): δ 1.53(d, CH₃, 3H), 2.48(s, CH₃, 3H), 3.95(s, OMe, 3H), 4.9(s, CH₂SO₂, 2H), 5.3(q, CHO, 1H), 7.2-7.6(m, ArH and NH, 5H) and 8.8(bs, NH, 1H).

$^{(d)}$PMR(CDCl₃, 200 MHz): δ 1.03(t, CH₃, 3H), 1.8-2.1(m/s, CH₃C(O) and CH₂, 5H), 2.33(s, Me, 3H), 3.84(s, OMe, 3H), 4.85 and 5.40(ABq, CH₂SO₂, 2H), 5.9(m, CH, 1H), 6.25(s, pyrm-H, 1H), 7.2-7.6(m, ArH, 4H), 7.8(bs, NH, 1H) and 12.65(bs, NH, 1H).

TEST A

Seeds of barley (*Hordeum vulgare*), barnyardgrass (*Echinochloa crus-galli*), cheatgrass (*Bromus secalinus*), cocklebur (*Xanthium pensylvanicum*), corn (*Zea mays*), cotton (*Gossypium hirsutum*), crabgrass (*Digitaria spp.*), giant foxtail (*Setaria faberi*), morningglory (*Ipomoea spp.*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a nonphytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| Rate (400 g/ha) | Compound Number | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| POSTEMERGENCE | | | | | | | | | | | | | | |
| Barley | 5 | 8 | 7 | 9 | 9 | 0 | 2 | 9 | 7 | 9 | 9 | 3 | 0 | 2 |
| Barnyardgrass | 9 | 9 | 0 | 9 | 9 | 2 | 2 | 6 | 9 | 9 | 9 | 0 | 0 | 3 |
| Cheatgrass | 7 | 8 | 8 | 9 | 9 | 8 | 4 | 6 | 8 | 9 | 9 | 7 | 7 | 8 |
| Cocklebur | 10 | 10 | 8 | 5 | 10 | 9 | 8 | 8 | 10 | 7 | 10 | 9 | 3 | 8 |
| Corn | 8 | 9 | 7 | 9 | 9 | 3 | 9 | 9 | 8 | 9 | 9 | 0 | 4 | 9 |
| Cotton | 9 | 9 | 8 | 9 | 9 | 8 | 5 | 9 | 9 | 9 | 10 | 9 | 0 | 4 |
| Crabgrass | — | — | 0 | — | 9 | 0 | 0 | 3 | 8 | 9 | 10 | 0 | 0 | 3 |
| Giant foxtail | 6 | 8 | 0 | 9 | 9 | 0 | 2 | 3 | 5 | 9 | 9 | 0 | 0 | 0 |
| Morningglory | 10 | 10 | 0 | 10 | 10 | 7 | 8 | 7 | 10 | 9 | 9 | 7 | 4 | 8 |
| Nutsedge | 9 | 9 | 5 | 9 | 9 | — | 8 | 7 | 8 | 9 | 9 | — | 0 | — |
| Rice | 7 | 9 | 8 | 9 | 9 | 6 | 8 | 8 | 5 | 9 | 9 | 0 | 0 | 7 |
| Sorghum | 9 | 9 | 8 | 9 | 9 | 7 | 9 | 9 | 9 | 9 | 9 | 0 | 9 | 9 |
| Soybean | 9 | 9 | 4 | 9 | 9 | 5 | 7 | 8 | 9 | 9 | 10 | 4 | 3 | 8 |
| Sugar beet | 9 | 10 | 9 | 9 | 10 | 9 | 9 | 9 | 9 | 10 | 10 | 8 | 8 | 8 |
| Velvetleaf | 10 | 10 | 1 | 9 | 10 | 8 | 1 | 6 | 10 | 7 | 9 | 2 | 0 | 0 |
| Wheat | 0 | 7 | 4 | 9 | 9 | 0 | 4 | 8 | 0 | 9 | 9 | 0 | 0 | 3 |
| Wild Oat | 5 | 8 | 3 | 9 | 9 | 0 | 0 | 8 | 7 | 9 | 9 | 0 | 0 | 2 |
| PREEMERGENCE | | | | | | | | | | | | | | |
| Barley | 2 | 7 | 8 | 9 | 9 | 0 | 7 | 7 | 4 | 9 | 9 | 0 | 3 | 2 |
| Barnyardgrass | 8 | 9 | 2 | 9 | 9 | 0 | 0 | 8 | 8 | 9 | 9 | 0 | 0 | 0 |
| Cheatgrass | 7 | 8 | 3 | 9 | 9 | 5 | 5 | 8 | 7 | 9 | 9 | 4 | 4 | 5 |
| Cocklebur | 9 | 9 | 1 | 1 | 8 | 4 | 4 | 7 | — | 8 | 9 | 6 | 2 | 4 |
| Corn | 9 | 9 | 9 | 9 | 9 | 0 | 7 | 8 | 8 | 9 | 9 | 0 | 3 | 3 |
| Cotton | 9 | 8 | 2 | 7 | 8 | 3 | 1 | 9 | 9 | 9 | 9 | 3 | 4 | 8 |
| Crabgrass | 8 | 5 | 2 | 9 | 9 | 0 | 8 | 5 | 8 | 9 | 9 | 9 | 9 | 4 |
| Giant foxtail | 0 | 6 | 0 | 9 | 9 | 0 | 0 | 8 | 4 | 9 | 10 | 0 | 3 | 3 |
| Morningglory | 9 | 8 | 1 | 7 | 9 | 3 | 7 | 8 | 9 | 9 | 9 | 4 | 3 | 9 |
| Nutsedge | 9 | 9 | 0 | 8 | 8 | 5 | 5 | 0 | 9 | 10 | 9 | 9 | 4 | 0 |
| Rice | 7 | 8 | 8 | 10 | 9 | 2 | 7 | 7 | 8 | 10 | 10 | 0 | 0 | 0 |

TABLE A-continued

| | | | | | | | | | | | | | | |
|---|---|---|---|---|---|---|---|---|---|---|---|---|---|---|
| Sorghum | 9 | 9 | 8 | 9 | 9 | 0 | 8 | 9 | 9 | 9 | 9 | 3 | 8 | 8 |
| Soybean | 9 | 8 | 3 | 9 | 9 | 2 | 5 | 6 | 9 | 9 | 9 | 5 | 2 | 6 |
| Sugar beet | 8 | 9 | 6 | 9 | 9 | 8 | 8 | 8 | 9 | 9 | 9 | 6 | 4 | 7 |
| Velvetleaf | 9 | 9 | 0 | 2 | 5 | 5 | 0 | 8 | 9 | 7 | 8 | 2 | 0 | 2 |
| Wheat | 0 | 7 | 7 | 8 | 9 | 0 | 6 | 6 | 3 | 9 | 9 | 0 | 0 | 0 |
| Wild Oat | 3 | 6 | 2 | 8 | 8 | 0 | 6 | 6 | 5 | 8 | 8 | 0 | 0 | 0 |

| | Compound Number | | | |
|---|---|---|---|---|
| Rate (200 g/ha) | 15 | 16 | 17 | 18 |
| POSTEMERGENCE | | | | |
| Barley | 3 | 8 | 2 | 9 |
| Barnyardgrass | 8 | 9 | 2 | 10 |
| Cheatgrass | 6 | 9 | 4 | 9 |
| Cocklebur | 10 | 9 | 8 | 10 |
| Corn | 7 | 9 | 2 | 10 |
| Cotton | 10 | 9 | 9 | 9 |
| Crabgrass | 6 | 5 | 0 | 9 |
| Giant foxtail | 4 | 8 | 1 | 9 |
| Morningglory | 10 | 9 | 9 | 0 |
| Nutsedge | 9 | 10 | 8 | 10 |
| Rice | 5 | 9 | 0 | 9 |
| Sorghum | 8 | 9 | 3 | 9 |
| Soybean | 9 | 9 | 8 | 9 |
| Sugar beet | 10 | 9 | 8 | 9 |
| Velvetleaf | 10 | 9 | 8 | 9 |
| Wheat | 0 | 5 | 0 | 9 |
| Wild Oat | 0 | 6 | 0 | 9 |
| PREEMERGENCE | | | | |
| Barley | 1 | 2 | 0 | 9 |
| Barnyardgrass | 7 | 8 | 5 | 9 |
| Cheatgrass | 5 | 7 | 2 | 8 |
| Cocklebur | 8 | 9 | 7 | — |
| Corn | 8 | 9 | 3 | 9 |
| Cotton | 8 | 7 | 7 | 8 |
| Crabgrass | 5 | 9 | 6 | 9 |
| Giant foxtail | 2 | 6 | 1 | 9 |
| Morningglory | 9 | 9 | 8 | 9 |
| Nutsedge | 9 | 7 | 3 | 7 |
| Rice | 7 | 8 | 3 | 10 |
| Sorghum | 8 | 9 | 3 | 9 |
| Soybean | 8 | 8 | 7 | 9 |
| Sugar beet | 8 | 9 | 8 | 9 |
| Velvetleaf | 9 | 7 | 7 | 7 |
| Wheat | 0 | 3 | 0 | 9 |
| Wild Oat | 0 | 7 | 0 | 8 |

| | Compound Number | | | | | | | | |
|---|---|---|---|---|---|---|---|---|---|
| Rate (100 g/ha) | 1 | 2 | 3 | 4 | 5 | 6 | 7 | 12 | 13 | 14 |
| POSTEMERGENCE | | | | | | | | | | |
| Barley | 2 | 7 | 0 | 8 | 8 | 0 | 0 | 0 | 0 | 0 |
| Barnyardgrass | 2 | 9 | 0 | 9 | 9 | 0 | 0 | 0 | 0 | 0 |
| Cheatgrass | 2 | 5 | 0 | 9 | 9 | 0 | 0 | 4 | 3 | 3 |
| Cocklebur | 10 | 9 | 1 | 5 | 9 | 7 | 2 | 7 | 0 | 2 |
| Corn | 5 | 9 | 2 | 9 | 9 | 0 | 5 | 0 | 1 | 3 |
| Cotton | 9 | 9 | 2 | 9 | 9 | 8 | 0 | 5 | 0 | 2 |
| Crabgrass | — | 2 | — | 9 | — | 0 | 0 | 0 | 0 | 0 |
| Giant foxtail | 0 | 3 | 0 | 8 | 9 | 0 | 0 | 0 | 0 | 0 |
| Morningglory | 10 | 10 | 0 | 9 | 10 | 5 | 2 | 3 | 1 | 4 |
| Nutsedge | 9 | 9 | 0 | 8 | 8 | 0 | 0 | 7 | — | — |
| Rice | 3 | 9 | 3 | 9 | 9 | 0 | 5 | 0 | 0 | 6 |
| Sorghum | 7 | 9 | 2 | 9 | 9 | 2 | 7 | 0 | 6 | 5 |
| Soybean | 9 | 9 | 5 | 9 | 9 | 4 | 1 | 3 | 2 | 2 |
| Sugar beet | 10 | 10 | 2 | 9 | 10 | 2 | 4 | 7 | 7 | 7 |
| Velvetleaf | 9 | 8 | 0 | 7 | 7 | 7 | 0 | 0 | 0 | 0 |
| Wheat | 0 | 0 | 0 | 9 | 9 | 0 | 0 | 0 | 0 | 0 |
| Wild Oat | 2 | 2 | 0 | 6 | 9 | 0 | 0 | 0 | 0 | 0 |
| PREEMERGENCE | | | | | | | | | | |
| Barley | 0 | 5 | 0 | 9 | 9 | 0 | 0 | 0 | 0 | 0 |
| Barnyardgrass | 0 | 6 | 0 | 5 | 9 | 0 | 0 | 0 | 0 | 0 |
| Cheatgrass | 5 | 7 | 0 | 7 | 8 | 2 | 0 | 2 | 0 | 3 |
| Cocklebur | 6 | 3 | 0 | 0 | 5 | — | 0 | 3 | 0 | 3 |
| Corn | 5 | 9 | 0 | 9 | 9 | 0 | 2 | 0 | 0 | 0 |
| Cotton | 7 | 1 | 0 | 2 | 7 | 0 | 0 | 0 | 0 | 3 |
| Crabgrass | 2 | 3 | 0 | 8 | 7 | 0 | 3 | 8 | 6 | 2 |
| Giant foxtail | 0 | 3 | 0 | 3 | 9 | 0 | 2 | 0 | 0 | 2 |
| Morningglory | 8 | 5 | 0 | 3 | 6 | 1 | 2 | 0 | 0 | 5 |
| Nutsedge | 9 | 0 | 0 | 0 | 4 | 0 | 0 | 0 | 0 | 0 |
| Rice | 6 | 8 | 0 | 9 | 8 | 0 | 0 | 0 | 0 | 0 |
| Sorghum | 8 | 9 | 0 | 9 | 9 | 0 | 5 | 0 | 5 | 6 |
| Soybean | 8 | 5 | 0 | 7 | 7 | 0 | 2 | 2 | 1 | 4 |

TABLE A-continued

| | | | | | | | | | | |
|---|---|---|---|---|---|---|---|---|---|---|
| Sugar beet | 9 | 9 | 0 | 8 | 3 | 5 | 3 | 3 | 2 | 2 |
| Velvetleaf | 8 | 2 | 0 | 1 | 2 | 2 | 0 | 0 | 0 | 0 |
| Wheat | 0 | 3 | 0 | 9 | 9 | 0 | 0 | 0 | 0 | 0 |
| Wild Oat | 0 | 0 | 0 | 7 | 4 | 0 | 0 | 0 | 0 | 0 |

| | Compound Number | | | | | | | | | | | | | | | | | | | | | |
|---|---|---|---|---|---|---|---|---|---|---|---|---|---|---|---|---|---|---|---|---|---|---|
| Rate (50 g/ha) | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| POSTEMERGENCE | | | | | | | | | | | | | | | | | | | | | | |
| Barley | 0 | 0 | 5 | 0 | 8 | 9 | 0 | 0 | 0 | 0 | 7 | 0 | 8 | 1 | 2 | 5 | 0 | 4 | 0 | 0 | 4 | 6 |
| Barnyardgrass | 0 | 0 | 0 | 2 | 8 | 9 | 0 | 0 | 0 | 2 | 8 | 0 | 9 | 5 | 3 | 6 | 2 | 8 | 0 | 0 | 7 | 9 |
| Cheatgrass | 0 | 0 | 0 | 2 | 8 | 9 | 0 | 0 | 3 | 2 | 8 | 0 | 9 | 3 | 7 | 4 | 5 | 8 | 2 | 2 | 7 | 7 |
| Cocklebur | 6 | 0 | 5 | 9 | 3 | 9 | 7 | 0 | 0 | 10 | 9 | 2 | 9 | 4 | 9 | 9 | 9 | 9 | 9 | 7 | 3 | 9 |
| Corn | 0 | 2 | 3 | 2 | 9 | 9 | 0 | 0 | 0 | 5 | 9 | 0 | 9 | 7 | 4 | 8 | 3 | 9 | 2 | 7 | 9 | 9 |
| Cotton | 3 | 0 | 2 | 9 | 8 | 9 | 6 | 0 | 0 | 9 | 9 | 8 | 9 | 0 | 9 | 9 | 9 | 8 | 9 | 9 | 9 | 9 |
| Crabgrass | 0 | 0 | — | — | — | — | 0 | 0 | 0 | 0 | 3 | 0 | 9 | 0 | 2 | 0 | 2 | 5 | 0 | 0 | 0 | 1 |
| Giant foxtail | 0 | 0 | 0 | 0 | 8 | 9 | 0 | 0 | 0 | 3 | 4 | 0 | 9 | 0 | 0 | 0 | 0 | 7 | 0 | 0 | 2 | 4 |
| Morningglory | 4 | 0 | 0 | 9 | 9 | 8 | 2 | 0 | 0 | 10 | 10 | 2 | 9 | 5 | 9 | 6 | 10 | 10 | 8 | 3 | 9 | 9 |
| Nutsedge | 0 | 0 | 0 | 10 | 0 | 6 | — | 0 | 0 | 9 | 9 | 0 | 9 | 0 | 9 | 9 | — | 9 | 10 | — | — | — |
| Rice | 0 | 3 | 5 | 2 | 9 | 9 | 0 | 0 | 0 | 0 | 8 | 0 | 9 | 5 | 3 | 6 | 0 | 7 | 3 | 3 | 9 | 9 |
| Sorghum | 0 | — | 5 | 8 | 9 | 9 | 0 | 6 | 5 | 5 | 9 | 2 | 9 | 8 | 9 | 7 | 7 | 8 | 4 | 4 | 9 | 9 |
| Soybean | 3 | 1 | — | 9 | 9 | 9 | 0 | 0 | 0 | 9 | 9 | 3 | 9 | 2 | 9 | 8 | 9 | 9 | 9 | 9 | 9 | 9 |
| Sugar beet | 4 | 4 | 8 | 9 | 8 | 7 | 7 | 5 | 6 | 10 | 9 | 2 | 9 | 8 | 9 | 5 | 9 | 7 | 4 | 3 | 9 | 9 |
| Velvetleaf | 2 | 0 | 2 | 9 | 5 | 6 | 0 | 0 | 0 | 10 | 9 | 0 | 9 | 0 | 9 | 5 | 9 | 9 | 9 | 0 | 6 | 6 |
| Wheat | 0 | 0 | 0 | 0 | 9 | 9 | 0 | 0 | 0 | 0 | 0 | 0 | 9 | 0 | 0 | 0 | 2 | 2 | 2 | 0 | 7 | 7 |
| Wild Oat | 0 | 0 | 2 | 0 | 8 | 7 | 0 | 0 | 0 | 0 | 3 | 0 | 8 | 0 | 0 | 3 | 0 | 3 | 2 | 0 | 3 | 7 |
| PREEMERGENCE | | | | | | | | | | | | | | | | | | | | | | |
| Barley | 0 | 0 | 2 | 0 | 8 | 9 | 0 | 0 | 0 | 0 | 3 | 0 | 8 | 0 | 0 | 2 | 0 | 0 | 0 | 0 | 6 | 7 |
| Barnyardgrass | 0 | 0 | 0 | 1 | 5 | 9 | 0 | 0 | 0 | 1 | 4 | 0 | 9 | 0 | 0 | 3 | 0 | 7 | 0 | 0 | 0 | 7 |
| Cheatgrass | 0 | 0 | 4 | 3 | 7 | 8 | 0 | 0 | 0 | 0 | 5 | 0 | 8 | 0 | 0 | 4 | 2 | 4 | 0 | 3 | 6 | 8 |
| Cocklebur | 0 | 0 | 1 | 6 | 3 | 9 | 2 | 0 | 0 | 5 | — | 3 | — | — | — | 5 | 5 | 8 | 5 | 1 | — | 5 |
| Corn | 0 | 0 | 3 | 0 | 7 | 9 | 0 | 0 | 0 | 5 | 9 | 0 | 9 | 0 | 3 | 4 | 0 | 6 | 0 | 4 | 8 | 9 |
| Cotton | 0 | 0 | 0 | 6 | 9 | 8 | 0 | 0 | 0 | 2 | 2 | 3 | 4 | 0 | 3 | 2 | 0 | 2 | 1 | 1 | 2 | 5 |
| Crabgrass | 0 | 0 | 0 | 5 | — | 5 | 7 | 6 | — | 0 | 5 | 0 | 9 | 0 | 0 | 2 | 3 | 0 | 3 | 3 | 0 | 2 |
| Giant foxtail | 0 | 0 | 2 | 0 | 6 | 9 | 0 | 0 | 2 | 0 | 0 | 0 | 9 | 0 | 0 | 0 | 2 | 0 | 0 | 2 | 0 | 2 |
| Morningglory | 0 | 0 | 0 | 6 | 7 | 8 | 0 | 0 | 1 | 9 | 4 | 5 | 8 | 0 | 4 | 3 | 9 | 6 | 0 | 1 | 4 | 7 |
| Nutsedge | 0 | 0 | 0 | 9 | 2 | 0 | 0 | 0 | 0 | 0 | 0 | 0 | 4 | 0 | — | 3 | 9 | 7 | 0 | — | 0 | 0 |
| Rice | 0 | 0 | 0 | 0 | 8 | 9 | 0 | 0 | 0 | 3 | 7 | 0 | 9 | 0 | 2 | 4 | 2 | 6 | 2 | 0 | 7 | 7 |
| Sorghum | 0 | 0 | 0 | 7 | 9 | 9 | 0 | 0 | 0 | 3 | 8 | 0 | 9 | 5 | 3 | 5 | 2 | 7 | 0 | 0 | 8 | 9 |
| Soybean | 0 | 0 | 2 | 6 | 8 | 9 | 0 | 0 | 0 | 5 | 6 | 0 | 8 | 2 | 4 | 6 | 3 | 7 | 2 | 2 | 6 | 7 |
| Sugar beet | 2 | 0 | 1 | 7 | 6 | 4 | 3 | 0 | 0 | 8 | 7 | 4 | 9 | 2 | 3 | 5 | 7 | 5 | 2 | 1 | 5 | 9 |
| Velvetleaf | 0 | 0 | 1 | 8 | 2 | 2 | 0 | 0 | 0 | 7 | 1 | 5 | 4 | 0 | 0 | 5 | 3 | 8 | 2 | 3 | 0 | 0 |
| Wheat | 0 | 0 | 2 | 0 | 7 | 8 | 0 | 0 | 0 | 0 | 0 | 0 | 8 | 0 | 0 | 0 | 0 | 0 | 0 | 0 | 7 | 8 |
| Wild Oat | 0 | 0 | 2 | 2 | 4 | 6 | 0 | 0 | 0 | 0 | 0 | 0 | 2 | 0 | 0 | 0 | 0 | 2 | 0 | 0 | 0 | 3 |

| | Compound Number | | | | | | | | |
|---|---|---|---|---|---|---|---|---|---|
| Rate (10 g/ha) | 19 | 20 | 21 | 22 | 23 | 24 | 25 | 26 | 27 |
| POSTEMERGENCE | | | | | | | | | |
| Barley | 0 | 0 | 1 | 0 | 0 | 0 | 0 | 0 | 2 |
| Barnyardgrass | 0 | 0 | 0 | 0 | 6 | 0 | 0 | 5 | 7 |
| Cheatgrass | 0 | 0 | 3 | 0 | 6 | 0 | 0 | 0 | 0 |
| Cocklebur | 1 | 7 | 2 | 9 | 7 | 7 | 3 | 0 | 9 |
| Corn | 2 | 1 | 4 | 0 | 7 | 0 | 3 | 9 | 7 |
| Cotton | 0 | 8 | 8 | 9 | 5 | 9 | 6 | 8 | 8 |
| Crabgrass | 0 | — | 0 | 0 | 0 | 0 | 0 | 0 | 0 |
| Giant foxtail | 0 | 0 | 0 | 0 | 1 | 0 | 0 | 0 | 0 |
| Morningglory | 0 | 6 | 5 | 10 | 8 | 1 | 1 | 8 | 9 |
| Nutsedge | 0 | — | — | 9 | 8 | 8 | 0 | 0 | 5 |
| Rice | 0 | 0 | 2 | 0 | 3 | 0 | 2 | 7 | 9 |
| Sorghum | 0 | 3 | 1 | 0 | 7 | 0 | 0 | 9 | 9 |
| Soybean | 0 | 9 | 9 | 7 | 9 | 9 | 9 | 8 | 7 |
| Sugar beet | 5 | 3 | 2 | 6 | 5 | 3 | 1 | 8 | 6 |
| Velvetleaf | 0 | 6 | 0 | 9 | 9 | 5 | 0 | — | 0 |
| Wheat | 0 | 0 | 0 | 0 | 0 | 0 | 0 | 2 | 2 |
| Wild Oat | 0 | 0 | 0 | 0 | 0 | 0 | 0 | 0 | 2 |
| PREEMERGENCE | | | | | | | | | |
| Barley | 0 | 0 | 0 | 0 | 0 | 0 | 0 | 0 | 2 |
| Barnyardgrass | 0 | 0 | 0 | 0 | 0 | 0 | 0 | 0 | 0 |
| Cheatgrass | 0 | 0 | 0 | 0 | 0 | 0 | 0 | 0 | 2 |
| Cocklebur | 0 | 0 | 0 | 2 | 0 | 0 | 0 | 0 | 0 |
| Corn | 0 | 0 | 0 | 0 | 3 | 0 | 0 | 3 | 6 |
| Cotton | 0 | 0 | 0 | 0 | 1 | 0 | 0 | 0 | 2 |
| Crabgrass | 0 | 0 | 0 | 0 | 0 | 0 | 0 | 0 | 2 |
| Giant foxtail | 0 | 0 | 0 | 0 | 0 | 0 | 0 | 0 | 0 |
| Morningglory | 0 | 0 | 0 | 0 | 0 | 0 | 0 | 0 | 5 |
| Nutsedge | 0 | — | 0 | 0 | 0 | — | 0 | 0 | 0 |
| Rice | 0 | 0 | 0 | 0 | 2 | 0 | 0 | 2 | 2 |
| Sorghum | 0 | 0 | 0 | 0 | 2 | 0 | 0 | 7 | 7 |
| Soybean | 0 | 0 | 0 | 0 | 2 | 0 | 0 | 2 | 4 |
| Sugar beet | 0 | 0 | 0 | 3 | 3 | 2 | 0 | 0 | 1 |
| Velvetleaf | 0 | 0 | 0 | 0 | 0 | 0 | 0 | 0 | 0 |

TABLE A-continued

| | | | | | | | | | |
|---|---|---|---|---|---|---|---|---|---|
| Wheat | 0 | 0 | 0 | 0 | 0 | 0 | 0 | 0 | 2 |
| Wild Oat | 0 | 0 | 0 | 0 | 0 | 0 | 0 | 0 | 0 |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria spp.*), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea spp.*), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. Plant response ratings, summarized in Table B, are based on a scale of 0 to 100 where 0 is no effect and 100 is complete control. A dash (-) response means no test result.

TABLE B

| | POSTEMERGENCE | | | | | | | | | | | |
|---|---|---|---|---|---|---|---|---|---|---|---|---|
| | Cmpd 1 | | | | Cmpd 4 | | | | Cmpd 5 | | | |
| Rate (g/ha) | 250 | 62 | 16 | 4 | 250 | 62 | 16 | 4 | 250 | 62 | 16 | 4 |
| Barley | 30 | 30 | 0 | 0 | 70 | 50 | 30 | 0 | 70 | 60 | 50 | 40 |
| Barnyardgrass | 60 | 40 | 30 | 0 | 80 | 50 | 50 | 0 | 100 | 70 | 60 | 30 |
| Blackgrass | 50 | 40 | 30 | 0 | 100 | 70 | 40 | 30 | 80 | 70 | 50 | 30 |
| Chickweed | 90 | 80 | 50 | 50 | 90 | 60 | 0 | 0 | 90 | 70 | 70 | 30 |
| Cocklebur | 90 | 80 | 60 | 30 | 60 | 0 | 0 | 0 | 90 | 70 | 60 | 0 |
| Corn | 50 | 30 | 0 | 0 | 90 | 70 | 60 | 40 | 100 | 70 | 60 | 50 |
| Cotton | 100 | 90 | 70 | 60 | 100 | 60 | 30 | 0 | 90 | 70 | 50 | 20 |
| Crabgrass | 30 | 0 | 0 | 0 | 100 | 80 | 30 | 0 | 90 | 80 | 30 | 0 |
| Downy brome | 30 | 20 | 0 | 0 | 70 | 50 | 30 | 0 | 70 | 50 | 30 | 0 |
| Giant foxtail | 40 | 30 | 0 | 0 | 90 | 50 | 0 | 0 | 90 | 70 | 50 | 0 |
| Green foxtail | 30 | 20 | 0 | 0 | 100 | 50 | 0 | 0 | 100 | 70 | 50 | 30 |
| Jimsonweed | 100 | 100 | 80 | 50 | 100 | 70 | 0 | 0 | 100 | 60 | 30 | 0 |
| Johnsongrass | 60 | 30 | 0 | 0 | 100 | 80 | 70 | 40 | 100 | 100 | 80 | 60 |
| Lambsquarters | 100 | 70 | 70 | 70 | 100 | 30 | 0 | 0 | 90 | 80 | 50 | 0 |
| Morningglory | 100 | 100 | 80 | 50 | 90 | 70 | 50 | 40 | 70 | 50 | 0 | 0 |
| Nutsedge | 100 | 100 | 100 | 70 | 100 | 50 | 30 | 0 | 100 | 70 | 30 | 0 |
| Rape | 100 | 100 | 70 | 60 | 100 | 70 | 50 | 0 | 90 | 70 | 30 | 0 |
| Rice | 0 | 0 | 0 | 0 | 80 | 70 | 50 | 30 | 80 | 60 | 50 | 30 |
| Sicklepod | 90 | 80 | 70 | 50 | 80 | 60 | 50 | 0 | 80 | 70 | 0 | 0 |
| Soybean | 100 | 90 | 80 | 70 | 90 | 70 | 60 | 50 | 90 | 70 | 60 | 50 |
| Sugar beet | 100 | 90 | 70 | 70 | 100 | 70 | 30 | 0 | 100 | 70 | 20 | 0 |
| Teaweed | 70 | 50 | 30 | 0 | 80 | 50 | 30 | 0 | 70 | 50 | 30 | 0 |
| Velvetleaf | 100 | 90 | 90 | 40 | 90 | 70 | 50 | 30 | 90 | 60 | 30 | 0 |
| Wheat | 0 | 0 | 0 | 0 | 60 | 30 | 20 | 0 | 60 | 50 | 0 | 0 |
| Wild buckwheat | 100 | 100 | 90 | 90 | 100 | 80 | 80 | 80 | 90 | 90 | 60 | 50 |
| Wild oat | 50 | 0 | 0 | 0 | 100 | 70 | 30 | 0 | 70 | 50 | 30 | 0 |

| | POSTEMERGENCE | | | | | | | | | | | |
|---|---|---|---|---|---|---|---|---|---|---|---|---|
| | Cmpd 9 | | | | Cmpd 11 | | | | Cmpd 15 | | | |
| Rate (g/ha) | 62 | 16 | 4 | 1 | 250 | 62 | 16 | 4 | 250 | 62 | 16 | 4 |
| Barley | 30 | 0 | 0 | 0 | 90 | 70 | 50 | 20 | 30 | 0 | 0 | 0 |
| Barnyardgrass | 50 | 40 | 30 | 30 | 100 | 90 | 80 | 50 | 60 | — | 0 | 0 |
| Blackgrass | 60 | 40 | 40 | 30 | 100 | 90 | 80 | 40 | 70 | 50 | 30 | 0 |
| Chickweed | 70 | 30 | 0 | 0 | 100 | 100 | 70 | 20 | 90 | 80 | 80 | 50 |
| Cocklebur | 80 | 70 | 40 | 0 | 100 | 100 | 80 | 0 | 100 | 100 | 100 | 40 |
| Corn | 70 | 20 | 10 | 0 | 100 | 100 | 90 | 70 | 60 | 40 | 30 | 0 |
| Cotton | 90 | 80 | 70 | 60 | 90 | 90 | 90 | 0 | 100 | 100 | 100 | 100 |
| Crabgrass | 50 | 50 | 30 | 0 | 100 | 90 | 50 | 20 | 50 | 30 | 30 | 0 |
| Downy brome | 40 | 0 | 0 | 0 | 100 | 80 | 50 | 20 | 0 | 0 | 0 | 0 |
| Giant foxtail | 50 | 45 | 20 | 20 | 90 | 60 | 40 | 0 | 30 | 0 | 0 | 0 |
| Green foxtail | 0 | 0 | 0 | 0 | 90 | 70 | 40 | 0 | 40 | 0 | 0 | 0 |
| Jimsonweed | 100 | 60 | 30 | 0 | 100 | 80 | 80 | 20 | 100 | 100 | 100 | 80 |
| Johnsongrass | 30 | 0 | 0 | 0 | 100 | 100 | 90 | 70 | 70 | 0 | 0 | 0 |
| Lambsquarters | 90 | — | — | 0 | 100 | 100 | — | 0 | 100 | 100 | 100 | 100 |
| Morningglory | 90 | 70 | 50 | 50 | 90 | 60 | 40 | 0 | 90 | 80 | 80 | 80 |
| Nutsedge | 100 | 100 | 60 | 40 | 80 | 70 | 50 | 0 | 100 | 100 | 100 | 70 |
| Rape | 100 | 100 | 60 | 40 | 100 | 100 | 90 | 80 | 100 | 100 | 100 | 100 |
| Rice | 30 | 0 | 0 | 0 | 100 | 100 | 90 | 50 | 40 | 0 | 0 | 0 |
| Sicklepod | 95 | 90 | 80 | 20 | 100 | 90 | 80 | 20 | 90 | 90 | 80 | 80 |
| Soybean | 100 | 100 | 95 | 80 | 100 | 100 | 90 | 80 | 100 | 90 | 90 | 80 |
| Sugar beet | 100 | 90 | 80 | 30 | 100 | 90 | 40 | 0 | 100 | 100 | 100 | 70 |
| Teaweed | 60 | 40 | 20 | 0 | 50 | 50 | 20 | 0 | 90 | 90 | 80 | 70 |
| Velvetleaf | 80 | 80 | 20 | 0 | 100 | 80 | 20 | 0 | 100 | 100 | 100 | 90 |
| Wheat | 0 | 0 | 0 | 0 | 90 | 80 | 40 | 20 | 0 | 0 | 0 | 0 |

TABLE B-continued

| | | | | | | | | | | | | |
|---|---|---|---|---|---|---|---|---|---|---|---|---|
| Wild buckwheat | 100 | 90 | 90 | 80 | 100 | 40 | 0 | 0 | 100 | 100 | 90 | 90 |
| Wild oat | 40 | 0 | 0 | 0 | 100 | 50 | 20 | 0 | 30 | 0 | 0 | 0 |

POSTEMERGENCE

| | Cmpd 16 | | | | Cmpd 18 | | | | Cmpd 22 | | | |
|---|---|---|---|---|---|---|---|---|---|---|---|---|
| Rate (g/ha) | 62 | 16 | 4 | 1 | 62 | 16 | 4 | 1 | 62 | 16 | 4 | 1 |
| Barley | 40 | 20 | 0 | 0 | 70 | 50 | 30 | 0 | 0 | 0 | 0 | 0 |
| Barnyardgrass | 40 | 20 | 0 | 0 | 100 | 90 | 70 | 40 | 30 | 0 | 0 | 0 |
| Blackgrass | 70 | 30 | 20 | 0 | 70 | 50 | 30 | 20 | 20 | 0 | 0 | 0 |
| Chickweed | 80 | 50 | 40 | 0 | 90 | 80 | 70 | 70 | 50 | 0 | 0 | 0 |
| Cocklebur | 90 | 90 | 70 | 20 | 100 | 100 | 90 | 80 | 100 | 100 | 80 | 40 |
| Corn | 90 | 80 | 60 | 30 | 100 | 90 | 90 | 70 | 20 | 0 | 0 | 0 |
| Cotton | 90 | 90 | 70 | 30 | 100 | 90 | 90 | 70 | 100 | 100 | 100 | 0 |
| Crabgrass | 30 | 0 | 0 | 0 | 90 | 80 | 50 | 0 | 0 | 0 | 0 | 0 |
| Downy brome | 60 | 40 | 20 | 0 | 80 | 70 | 70 | 50 | 20 | 0 | 0 | 0 |
| Giant foxtail | 60 | 40 | 20 | 0 | 100 | 90 | 40 | 30 | 0 | 0 | 0 | 0 |
| Green foxtail | 30 | 20 | 0 | 0 | 100 | 90 | 60 | 40 | 0 | 0 | 0 | 0 |
| Jimsonweed | 100 | 100 | 100 | 50 | 90 | 90 | 90 | 90 | 100 | 80 | 70 | 70 |
| Johnsongrass | 40 | 20 | 0 | 0 | 100 | 100 | 80 | 50 | 0 | 0 | 0 | 0 |
| Lambsquarters | 100 | 100 | 100 | 50 | 100 | 100 | 80 | 80 | 100 | 70 | 60 | 50 |
| Morningglory | 100 | 90 | 50 | 20 | 90 | 90 | 80 | 80 | 100 | 100 | 100 | 60 |
| Nutsedge | 80 | 80 | 70 | 50 | 90 | 90 | 30 | 0 | 100 | 100 | 70 | 40 |
| Rape | 100 | 100 | 100 | 70 | 100 | 100 | 100 | 90 | 100 | 100 | 100 | 95 |
| Rice | 60 | 40 | 20 | 0 | 100 | 90 | 70 | 30 | 0 | 0 | 0 | 0 |
| Sicklepod | 100 | 80 | 40 | 0 | 90 | 90 | 50 | 30 | 100 | 80 | 80 | 0 |
| Soybean | 100 | 90 | 90 | 60 | 100 | 90 | 90 | 70 | 100 | 100 | 100 | 40 |
| Sugar beet | 100 | 100 | 100 | 50 | 100 | 100 | 100 | 100 | 100 | 80 | 70 | 0 |
| Teaweed | 90 | 20 | 0 | 0 | 70 | 30 | 20 | 0 | 90 | 60 | 30 | 0 |
| Velvetleaf | 100 | 100 | 100 | 100 | 100 | 100 | 90 | 30 | 80 | 80 | 80 | 45 |
| Wheat | 40 | 20 | 0 | 0 | 70 | 40 | 20 | 0 | 0 | 0 | 0 | 0 |
| Wild buckwheat | 100 | 100 | 90 | 80 | 100 | 90 | 90 | 80 | 100 | 90 | 70 | 30 |
| Wild oat | 30 | 20 | 0 | 0 | 70 | 40 | 20 | 0 | 0 | 0 | 0 | 0 |

PREEMERGENCE

| | Cmpd 1 | | | | Cmpd 4 | | | | Cmpd 5 | | | |
|---|---|---|---|---|---|---|---|---|---|---|---|---|
| Rate (g/ha) | 250 | 62 | 16 | 4 | 250 | 62 | 16 | 4 | 250 | 62 | 16 | 4 |
| Barley | 0 | 0 | 0 | 0 | 100 | 30 | 0 | 0 | 100 | 40 | 0 | 0 |
| Barnyardgrass | 30 | 20 | 0 | 0 | 90 | 40 | 0 | 0 | 100 | 0 | 0 | 0 |
| Blackgrass | 40 | 30 | — | — | 100 | 90 | 40 | 0 | 80 | 30 | 30 | 0 |
| Chickweed | 100 | 100 | 95 | 90 | 100 | 90 | 0 | 0 | 90 | 70 | — | 65 |
| Cocklebur | 80 | 80 | — | 60 | 80 | 0 | 0 | 0 | 90 | 50 | 20 | — |
| Corn | 30 | 0 | 0 | 0 | 90 | 30 | 0 | 0 | 90 | 20 | 20 | 0 |
| Cotton | 80 | 60 | 0 | 0 | 40 | 20 | 0 | 0 | 80 | 0 | 0 | 0 |
| Crabgrass | 100 | 40 | 0 | — | 100 | 100 | 40 | 0 | 100 | 90 | 50 | 40 |
| Downy brome | 40 | 0 | 0 | 0 | 100 | 30 | 0 | 0 | 100 | 50 | 0 | 0 |
| Giant foxtail | 20 | 0 | 0 | 0 | 100 | 50 | 0 | 0 | 100 | 60 | 50 | 0 |
| Green foxtail | 20 | 0 | 0 | 0 | 100 | 40 | 20 | 0 | 100 | 70 | 60 | 0 |
| Jimsonweed | 100 | 50 | 0 | 0 | 90 | 50 | 0 | 0 | 50 | 0 | 0 | — |
| Johnsongrass | 30 | 0 | 0 | 0 | 100 | 50 | 30 | 30 | 90 | 55 | 0 | 0 |
| Lambsquarters | 100 | 100 | 100 | 100 | 100 | 100 | 80 | — | 100 | 100 | 100 | 0 |
| Morningglory | 90 | 70 | 30 | 0 | 100 | 0 | 0 | 0 | 40 | 0 | 0 | 0 |
| Nutsedge | 100 | 50 | 0 | 0 | 90 | 40 | 40 | 0 | 50 | 0 | 0 | 0 |
| Rape | 100 | 90 | 80 | 40 | 100 | 50 | 30 | 30 | 100 | 60 | 0 | 0 |
| Rice | 40 | 0 | 0 | 0 | 100 | 60 | 0 | 0 | 100 | 60 | 10 | 0 |
| Sicklepod | 100 | 60 | 0 | 0 | 80 | 40 | 0 | 0 | 30 | 0 | 0 | 0 |
| Soybean | 50 | 20 | 0 | 0 | 70 | 30 | 20 | 20 | 70 | 0 | 0 | 0 |
| Sugar beet | 100 | 90 | 80 | 50 | 100 | 80 | 30 | 30 | 100 | 70 | 0 | 0 |
| Teaweed | 90 | 50 | 30 | 0 | 60 | 55 | 0 | 0 | 40 | 0 | 0 | 0 |
| Velvetleaf | 100 | 0 | 0 | 0 | 40 | 20 | 0 | 0 | 60 | 30 | 0 | 0 |
| Wheat | 0 | 0 | 0 | 0 | 100 | 0 | 0 | 0 | 90 | 0 | 0 | 0 |
| Wild buckwheat | 100 | 100 | 90 | 70 | 100 | 80 | 35 | 30 | 100 | 30 | 0 | 0 |
| Wild oat | 0 | 0 | 0 | 0 | 60 | 30 | 0 | 0 | 70 | 20 | 0 | 0 |

PREEMERGENCE

| | Cmpd 9 | | | | Cmpd 11 | | | | Cmpd 15 | | | |
|---|---|---|---|---|---|---|---|---|---|---|---|---|
| Rate (g/ha) | 62 | 16 | 4 | 1 | 250 | 62 | 16 | 4 | 250 | 62 | 16 | 4 |
| Barley | 0 | 0 | 0 | 0 | 90 | 50 | 20 | 0 | 0 | 0 | 0 | 0 |
| Barnyardgrass | 0 | 0 | 0 | 0 | 90 | 50 | 40 | 30 | 35 | 30 | 0 | 0 |
| Blackgrass | 30 | 30 | 0 | 0 | 80 | 70 | 50 | 50 | 0 | 0 | 0 | 0 |
| Chickweed | 70 | 50 | 30 | 0 | 80 | 40 | 30 | 30 | 100 | 100 | 100 | 100 |
| Cocklebur | 70 | 50 | 40 | 30 | 90 | 90 | 50 | 20 | 100 | 80 | 40 | 30 |
| Corn | 50 | — | 0 | 0 | 100 | 70 | 20 | 0 | 80 | 20 | 0 | 0 |
| Cotton | 60 | 30 | 30 | 0 | 90 | 80 | 70 | 20 | 30 | 20 | 0 | 0 |
| Crabgrass | 50 | 30 | 0 | 0 | 100 | 100 | 90 | 30 | 85 | 80 | 70 | 65 |
| Downy brome | 40 | 30 | 0 | 0 | 90 | 80 | 40 | 0 | 0 | 0 | 0 | 0 |
| Giant foxtail | 30 | 0 | 0 | 0 | 90 | 80 | 60 | 50 | 50 | 0 | 0 | 0 |
| Green foxtail | 30 | 0 | 0 | 0 | 90 | 90 | 60 | 30 | 60 | 20 | 0 | 0 |
| Jimsonweed | 30 | 30 | 0 | 0 | 90 | 80 | 50 | 0 | 100 | 100 | 40 | 40 |
| Johnsongrass | 30 | 0 | 0 | 0 | 90 | 90 | 80 | 50 | 0 | 0 | 0 | 0 |
| Lambsquarters | 90 | 30 | 0 | 0 | 100 | 100 | 100 | 100 | 100 | 100 | 100 | 100 |
| Morningglory | 50 | 30 | 0 | 0 | 100 | 30 | 0 | 0 | 90 | 90 | 50 | 50 |

TABLE B-continued

| | | | | | | | | | | | | |
|---|---|---|---|---|---|---|---|---|---|---|---|---|
| Nutsedge | 80 | 50 | 0 | 0 | 90 | 70 | 30 | 0 | 100 | 80 | 0 | 0 |
| Rape | 70 | 40 | 30 | 0 | 90 | 30 | 20 | 0 | 100 | 100 | 90 | 40 |
| Rice | 0 | 0 | 0 | 0 | 100 | 90 | 70 | 30 | 50 | 30 | 0 | 0 |
| Sicklepod | 30 | 30 | 0 | 0 | 80 | 60 | 30 | 0 | 100 | 90 | 30 | 0 |
| Soybean | 60 | 20 | 0 | 0 | 90 | 70 | 20 | 0 | 100 | 40 | 20 | 20 |
| Sugar beet | 30 | 0 | 0 | 0 | 100 | 30 | 20 | 0 | 100 | 100 | 90 | 70 |
| Teaweed | 50 | 30 | 0 | 0 | 70 | 60 | 30 | 0 | 100 | 90 | 80 | 30 |
| Velvetleaf | 50 | 40 | 30 | 30 | 80 | 40 | 20 | 0 | 100 | 80 | 60 | 40 |
| Wheat | 0 | 0 | 0 | 0 | 70 | 40 | 20 | 0 | 0 | 0 | 0 | 0 |
| Wild buckwheat | 70 | 50 | 30 | 0 | 90 | 90 | 50 | 20 | 100 | 100 | 95 | 90 |
| Wild oat | 30 | 30 | 0 | 0 | 60 | 30 | 30 | 20 | 50 | 40 | 0 | 0 |

PREEMERGENCE

| | Cmpd 16 | | | | Cmpd 18 | | | | Cmpd 22 | | | |
|---|---|---|---|---|---|---|---|---|---|---|---|---|
| Rate (g/ha) | 62 | 16 | 4 | 1 | 62 | 16 | 4 | 1 | 62 | 16 | 4 | 1 |
| Barley | 20 | 0 | 0 | 0 | 30 | 30 | 20 | 0 | 0 | 0 | 0 | 0 |
| Barnyardgrass | 50 | 20 | 0 | 0 | 90 | 60 | 20 | 0 | 0 | 0 | 0 | 0 |
| Blackgrass | 30 | 20 | 0 | 0 | 30 | 20 | 0 | 0 | 30 | 0 | 0 | 0 |
| Chickweed | 30 | 20 | 0 | 0 | 90 | 70 | 30 | 0 | 70 | 50 | 30 | 0 |
| Cocklebur | 70 | 20 | 0 | 0 | 90 | 80 | 50 | 20 | 70 | 60 | 50 | 0 |
| Corn | 0 | 0 | 0 | 0 | 90 | 30 | 20 | 0 | 20 | 0 | 0 | 0 |
| Cotton | 20 | 0 | 0 | 0 | 90 | 30 | 20 | 0 | 40 | 30 | 0 | 0 |
| Crabgrass | 80 | 30 | 20 | 0 | 90 | 90 | 70 | 30 | 60 | 40 | 30 | 0 |
| Downy brome | 20 | 0 | 0 | 0 | 90 | 50 | 20 | 0 | 0 | 0 | 0 | 0 |
| Giant foxtail | 70 | 20 | 0 | 0 | 80 | 80 | 70 | 20 | 0 | 0 | 0 | 0 |
| Green foxtail | 90 | 20 | 0 | 0 | 90 | 80 | 70 | 30 | 30 | 0 | 0 | 0 |
| Jimsonweed | 50 | 20 | 0 | 0 | 90 | 30 | 20 | 0 | 90 | 60 | 30 | 0 |
| Johnsongrass | 80 | 30 | 0 | 0 | 90 | 80 | 50 | 0 | 0 | 0 | 0 | 0 |
| Lambsquarters | 80 | 50 | 50 | 30 | 100 | 90 | 30 | 0 | — | — | — | — |
| Morningglory | 70 | 20 | 0 | 0 | 90 | 80 | 30 | 0 | 90 | 60 | 0 | 0 |
| Nutsedge | 30 | 20 | 0 | 0 | 30 | 0 | 0 | 0 | 100 | 100 | 100 | 0 |
| Rape | 80 | 50 | 20 | 0 | 90 | 50 | 20 | 0 | 80 | 60 | 30 | 0 |
| Rice | 90 | 70 | 20 | 0 | 90 | 90 | 60 | 30 | 0 | 0 | 0 | 0 |
| Sicklepod | 80 | 30 | 0 | 0 | 90 | 90 | 80 | 20 | 60 | 30 | — | 0 |
| Soybean | 20 | 0 | 0 | 0 | 50 | 20 | 0 | 0 | 70 | 30 | 0 | 0 |
| Sugar beet | 30 | 20 | 0 | 0 | 90 | 90 | 30 | 0 | 90 | 70 | 60 | 60 |
| Teaweed | 50 | 30 | 0 | 0 | 90 | 30 | 20 | 0 | 70 | 30 | 0 | 0 |
| Velvetleaf | 50 | 30 | 0 | 0 | 90 | 80 | 70 | 70 | 60 | 30 | 30 | 0 |
| Wheat | — | — | 0 | 0 | 80 | 30 | 0 | 0 | 0 | 0 | 0 | 0 |
| Wild buckwheat | 90 | 80 | 30 | 0 | 90 | 80 | 70 | 20 | 90 | 60 | 0 | 0 |
| Wild oat | 0 | 0 | 0 | 0 | 60 | 50 | 20 | 0 | 0 | 0 | 0 | 0 |

TEST C

Plastic pots were partially filled with silt loam soil. The soil was then saturated with water. Indica and Japonica rice (*Oryza sativa*) seedlings at the 2.0 to 2.5 leaf stage, seeds of barnyardgrass (*Echinochloa crusgalli*), bulrush (*Scirpus mucronatus*), duck salad (*Heteranthera limosa*), and umbrella sedge (*Cyperus difformis*), and sprouted tubers of arrowhead (*Sagittaria spp.*) or waterchestnut (*Eleocharis spp.*) were planted into this soil. Several days after planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are based on a scale of 0 to 100 where 0 is no effect and 100 is complete control.

TABLE C

| Rate (g/ha) | 125 | 64 | 32 | 16 | 8 |
|---|---|---|---|---|---|
| Cmpd 9 | | | | | |
| Arrowhead | 95 | 90 | 90 | 70 | 60 |
| Barnyardgrass | 50 | 0 | 0 | 0 | 0 |
| Bulrush | 90 | 95 | 80 | 0 | 0 |
| Duck salad | 100 | 100 | 100 | 90 | 0 |
| Indica rice | 30 | 30 | 0 | 0 | 0 |
| Japonica rice | 30 | 20 | 0 | 0 | 0 |
| Umbrella sedge | 100 | 100 | 100 | 100 | 90 |
| Cmpd 15 | | | | | |
| Arrowhead | 95 | 95 | 95 | 95 | 90 |
| Barnyardgrass | 70 | 60 | 50 | 50 | 40 |
| Bulrush | 95 | 95 | 95 | 90 | 80 |
| Duck salad | 100 | 100 | 100 | 100 | 100 |
| Indica rice | 0 | 0 | 0 | 0 | 0 |
| Japonica rice | 30 | 20 | 0 | 0 | 0 |
| Umbrella sedge | 100 | 100 | 100 | 100 | 95 |
| Cmpd 22 | | | | | |
| Barnyardgrass | 70 | 60 | 50 | 30 | 20 |
| Bulrush | 90 | 90 | 90 | 90 | 90 |
| Duck salad | 100 | 100 | 100 | 100 | 100 |
| Indica rice | 0 | 0 | 0 | 0 | 0 |
| Japonica rice | 20 | 0 | 0 | 0 | 0 |
| Umbrella sedge | 98 | 98 | 98 | 95 | 95 |
| Waterchestnut | 98 | 95 | 80 | 80 | 70 |

TEST D

Seeds of spring and winter barley (*Hordeum vulgare*), black nightshade (*Solanum nigrum*), blackgrass (*Alopecurus myosuroides*), bluegrass (*Poa annua*), catchweed bedstraw (*Galium aparine*), cheatgrass (*Bromus secalinus*), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hederaefolia*), jointed goatgrass (*Aegilops cylindrica*), kochia (*Kochia scoparia*), lambsquarters (*Chenopodium album*), Persian speedwell (*Veronica persica*), rape (*Brassica napus*), Russian thistle (*Salsola kali*), scentless chamomile (*Matricaria inodora*), sugar beat (*Beta vulgaris*), spring and winter wheat (*Triticum aestivum*), wild buckwheat (*Polygonum convolvulus*), and wild oat (*Avena fatua*) were planted and treated preemergence with test chemical dissolved in a non-phytotoxic solvent. These crop and weed species were also treated with postemergence applications of the test chemical. Plants ranged in height from two to twenty-four cm for postemergence treatments. Blackgrass and wild oat were treated postemergence at two growth stages. The first stage was while the plants had one to three leaves; whereas the second stage was while the plants were beginning to tiller. Treated plants and controls were maintained in a greenhouse for approximately 21 days, after which all species were compared to controls and visually evaluated. Plant response ratings, summarized in Table D, are based on a scale of 0 to 100 where 0 is no effect and 100 is complete control.

TABLE D

|  | Cmpd 15 | | | | |
| --- | --- | --- | --- | --- | --- |
| Rate (g/ha) | 125 | 64 | 32 | 16 | 8 |
| POSTEMERGENCE | | | | | |
| Barley (Spring) | 20 | 20 | 10 | 0 | 0 |
| Barley (Winter) | 20 | 10 | 0 | 0 | 0 |
| Black nightshade | 60 | 60 | 60 | 0 | 0 |
| Blackgrass (Stage 1) | 0 | 0 | 0 | 0 | 0 |
| Blackgrass (Stage 2) | 20 | 0 | 0 | 0 | 0 |
| Bluegrass | 0 | 0 | 0 | 0 | 0 |
| Catchweed bedstraw | 100 | 100 | 80 | 70 | 50 |
| Cheatgrass | 0 | 0 | 0 | 0 | 0 |
| Downy brome | 0 | 0 | 0 | 0 | 0 |
| Field pennycress | 100 | 100 | 100 | 100 | 100 |
| Field violet | 90 | 60 | 60 | 40 | 20 |
| Green foxtail | 20 | 10 | 0 | 0 | 0 |
| Italian ryegrass | 0 | 0 | 0 | 0 | 0 |
| Ivyleaf speedwell | 80 | 80 | 60 | 20 | 0 |
| Jointed goatgrass | 0 | 0 | 0 | 0 | 0 |
| Kochia | 100 | 80 | 50 | 50 | 30 |
| Lambsquarters | 100 | 70 | 70 | 60 | 30 |
| Persian speedwell | 60 | 40 | 40 | 10 | 0 |
| Rape | 100 | 100 | 100 | 100 | 100 |
| Russian thistle | 100 | 90 | 80 | 50 | 20 |
| Scentless chamomile | 100 | 100 | 90 | 80 | 70 |
| Sugar beet | 100 | 100 | 100 | 100 | 90 |
| Wheat (Spring) | 20 | 10 | 0 | 0 | 0 |
| Wheat (Winter) | 20 | 10 | 0 | 0 | 0 |
| Wild buckwheat | 100 | 70 | 70 | 60 | 60 |
| Wild oat (Stage 1) | 20 | 0 | 0 | 0 | 0 |
| Wild oat (Stage 2) | 20 | 0 | 0 | 0 | 0 |
| PREEMERGENCE | | | | | |
| Barley (Spring) | 40 | 40 | 30 | 10 | 10 |
| Barley (Winter) | 20 | 20 | 10 | 10 | 0 |
| Black nightshade | 30 | 20 | 20 | 10 | 0 |
| Blackgrass | 20 | 20 | 0 | 0 | 0 |
| Bluegrass | 20 | 10 | 0 | 0 | 0 |
| Catchweed bedstraw | 90 | 70 | 70 | 60 | 20 |
| Cheatgrass | 30 | 30 | 20 | 0 | 0 |
| Downy brome | 0 | 0 | 0 | 0 | 0 |
| Field pennycress | 100 | 100 | 100 | 100 | 100 |
| Field violet | 100 | 100 | 70 | 40 | 20 |
| Green foxtail | 0 | 0 | 0 | 0 | 0 |
| Italian ryegrass | 0 | 0 | 0 | 0 | 0 |
| Ivyleaf speedwell | 90 | 90 | 30 | 20 | 0 |
| Jointed goatgrass | 10 | 0 | 0 | 0 | 0 |
| Kochia | 60 | 40 | 20 | 10 | 0 |
| Lambsquarters | 100 | 100 | 80 | 70 | 70 |
| Persian speedwell | 90 | 80 | 60 | 50 | 50 |
| Rape | 100 | 100 | 100 | 80 | 80 |
| Russian thistle | 30 | 10 | 0 | 0 | 0 |
| Scentless chamomile | 100 | 100 | 90 | 90 | 80 |
| Sugar beet | 100 | 90 | 80 | 80 | 70 |
| Wheat (Spring) | 0 | 0 | 0 | 0 | 0 |
| Wheat (Winter) | 0 | 0 | 0 | 0 | 0 |
| Wild buckwheat | 70 | 60 | 50 | 30 | 10 |
| Wild oat | 0 | 0 | 0 | 0 | 0 |

What is claimed is:

1. A compound of the formula

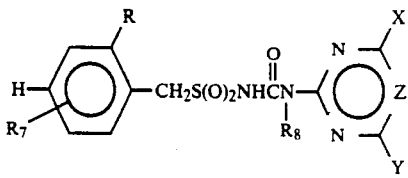

wherein
R is $C(OH)R_1R_2$, $C(OR_3)R_2R_4$, $C(O)R_1$ or $C(OR_5)(OR_6)R_4$;
$R_1$ is $C_1-C_3$ alkyl, $C_1-C_2$ haloalkyl or $C_1-C_2$ alkyl substituted by one of $OCH_3$, $SCH_3$ or CN;
$R_2$ is H or $CH_3$;
$R_3$ is C(O) ($C_1-C_3$ alkyl), C(O)cyclopropyl, $S(O)_2(C_1-C_3$ alkyl) or C(O)phenyl;
$R_4$ is H, $C_1-C_3$ alkyl, $C_1-C_2$ haloalkyl or $C_1-C_2$ alkyl substituted by one of $OCH_3$, $SCH_3$ or CN;
$R_5$ and $R_6$ are independently $C_1-C_2$ alkyl;
$R_7$ is H, $CH_3$, $CF_3$, F, Cl, Br, $NO_2$, $OCH_3$ or $SCH_3$;
$R_8$ is H or $CH_3$;
X is $C_1-C_2$ alkyl, $C_1-C_2$ alkoxy, $C_1-C_2$ haloalkoxy, $CH_2OCH_3$ or Cl;
Y is $C_1-C_2$ alkyl, $C_1-C_2$ alkoxy, $NHCH_3$ or $N(CH_3)_2$; and
Z is CH;
and their agriculturally suitable salts.

2. The compounds of claim 1 wherein $R_9$ is H; X is $CH_3$ or $OCH_3$; and Y is $CH_3$ or $OCH_3$.

3. The compounds of claim 2 wherein $R_3$ is $C(O)CH_3$, or $S(O)_2CH_3$.

4. The compounds of claim 3 wherein $R_1$ is $C_1-C_3$ alkyl; $R_4$ is $C_1-C_3$ alkyl; and $R_7$ is H.

5. The compound of claim 1 which is 2-[1-(Acetyloxy)ethyl]-N-[[(4,6-dimethoxy-2-pyrimidinyl)amino]carbonyl]benzenemethanesulfonamide.

6. The compound of claim 1 which is 2-Acetyl-N-[[(4,6-dimethoxy-2-pyrimidinyl)amino]carbonyl]benzenemethanesulfonamide.

7. The compound of claim 1 which is N-[[(4,6-dimethoxy-2-pyrimidinyl)amino]carbonyl]-2-(1-hydroxyethyl)benzenemethanesulfonamide.

8. An agriculturally suitable composition for controlling the growth of undesired vegetation comprising an effective amount of a compound of claim 1 and at least one of the following: surfactant, solid diluent or liquid diluent.

9. An agriculturally suitable composition for controlling the growth of undesired vegetation comprising an effective amount of a compound of claim 2 and at least one of the following: surfactant, solid diluent or liquid diluent.

10. An agriculturally suitable composition for controlling the growth of undesired vegetation comprising an effective amount of a compound of claim 3 and at least one of the following: surfactant, solid diluent or liquid diluent.

11. An agriculturally suitable composition for controlling the growth of undesired vegetation comprising an effective amount of a compound of claim 4 and at least one of the following: surfactant, solid diluent or liquid diluent.

12. An agriculturally suitable composition for controlling the growth of undesired vegetation comprising an effective amount of a compound of claim 5 and at least one of the following: surfactant, solid diluent or liquid diluent.

13. An agriculturally suitable composition for controlling the growth of undesired vegetation comprising an effective amount of a compound of claim 6 and at least one of the following: surfactant, solid diluent or liquid diluent.

14. An agriculturally suitable composition for controlling the growth of undesired vegetation comprising an effective amount of a compound of claim 7 and at least one of the following: surfactant, solid diluent o liquid diluent.

15. A method for controlling the growth of desired vegetation which comprises applying to the locus to be protected an effective amount of a compound of claim 1.

16. A method for controlling the growth of desired vegetation which comprises applying to the locus to be protected an effective amount of a compound of claim 2.

17. A method for controlling the growth of desired vegetation which comprises applying to the locus to be protected an effective amount of a compound of claim 3.

18. A method for controlling the growth of desired vegetation which comprises applying to the locus to be protected an effective amount of a compound of claim 4.

19. A method for controlling the growth of desired vegetation which comprises applying to the locus to be protected an effective amount of a compound of claim 5.

20. A method for controlling the growth of desired vegetation which comprises applying to the locus to be protected an effective amount of a compound of claim 6.

21. A method for controlling the growth of desired vegetation which comprises applying to the locus to be protected an effective amount of a compound of claim 7.

* * * * *